(12) United States Patent
Watts et al.

(10) Patent No.: US 9,050,374 B2
(45) Date of Patent: Jun. 9, 2015

(54) INHIBITORS AGAINST ENDOSOMAL/LYSOSOMAL ENZYMES

(75) Inventors: Colin Watts, Dundee (GB); Sander Van Kasteren, Amsterdam (NL)

(73) Assignee: UNIVERSITY COURT OF THE UNIVERSITY OF DUNDEE, Dundee (GB)

(*) Notice: Subject to any disclaimer, the term of this patent is extended or adjusted under 35 U.S.C. 154(b) by 0 days.

(21) Appl. No.: 14/239,354

(22) PCT Filed: Aug. 15, 2012

(86) PCT No.: PCT/GB2012/000660
§ 371 (c)(1),
(2), (4) Date: Feb. 18, 2014

(87) PCT Pub. No.: WO2013/024243
PCT Pub. Date: Feb. 21, 2013

(65) Prior Publication Data
US 2014/0308318 A1    Oct. 16, 2014

(30) Foreign Application Priority Data

Aug. 15, 2011   (GB) .................................. 1114017.5

(51) Int. Cl.
| | |
|---|---|
| C07K 7/06 | (2006.01) |
| A61K 47/48 | (2006.01) |
| A61K 38/57 | (2006.01) |
| C07K 14/81 | (2006.01) |
| A61K 38/18 | (2006.01) |
| A61K 39/39 | (2006.01) |
| C07K 14/47 | (2006.01) |
| A61K 39/00 | (2006.01) |

(52) U.S. Cl.
CPC ........... *A61K 47/48346* (2013.01); *A61K 38/57* (2013.01); *C07K 14/8139* (2013.01); *C07K 14/8142* (2013.01); *C07K 2319/00* (2013.01); *A61K 38/18* (2013.01); *A61K 38/1808* (2013.01); *A61K 39/39* (2013.01); *A61K 2039/55516* (2013.01); *C07K 7/06* (2013.01); *C07K 14/4703* (2013.01)

(58) Field of Classification Search
None
See application file for complete search history.

(56) References Cited

U.S. PATENT DOCUMENTS 7,709,446 B2 * 5/2010 Barr et al. .................... 514/20.2

FOREIGN PATENT DOCUMENTS

GB          EP1066315 A1      9/1999

OTHER PUBLICATIONS

Krol et al. Novel Bi- and Trifunctional Inhibitors of Tumor Associated Proteolytic Systems. Chem. Biol (2003) 384, 1086-1096.*
Krol et al. Inhibition of Intraperitoneal Tumor Growth of Human Ovarian Cancer Cells by Bi- and Trifunctional Inhibitors of Tumor Associated Proteolytic Systems. Chem. Biol (2003) 384, 1097-1102.*
Magnus Abrahamson et al., "Cystatins", "Biochemical Society Symposium: Proteases and the Regulation of Biological Processes", 2002, pp. 179-199, vol. 70, Publisher: Biochemical Society, Published in: http://symposia.biochemistry.org/bssymp/070/bss0700179.htm.
Marcia Alvarez-Fernandez et al., "Inhibition of Mammalian Legumain by Some Cystatins is Due to a Novel Second Reactive Site", "Journal of Biological Chemistry", 1999, pp. 19195-19203, vol. 274, Publisher: The American Society for Biochemistry and Molecular Biology, Inc., Published in: http://www.jbc.org/content/247/27/19195.
Ennes A. Auerswald et al., "Hairpin Loop Mutations of Chicken Cystatin Have Different Effects on the Inhibition of Cathepsin B, Cathepsin L and . . . ", "FEBS Letters", 1995, pp. 179-184, vol. 361, No. 2-3, Publisher: Federation of European Biochemical Societies, Published in: http://www.febsletters.org/article/0014-5793&2895%2900175-9/pdf.
Eric Bednarski et al., "Suppression of Cathepsins B and L Causes a Proliferation of Lysosomes and the Formation of Meganeurites in Hippocampus", "Journal of Neuroscience", 1997, pp. 4006-4021, vol. 17, No. 11, Publisher: Society for Neuroscience, Published in: http://www.jneurosci.org/content/17/11/4006.full.pdf+html.
Ingemar Bjork et al., "The Importance of the Second Hairpin Loop of Cystatin C for Proteinase Binding: Characterization of the Interation . . . ", "Biochemistry", 1996, pp. 10720-10726, vol. 35, No. 33, Publisher: American Chemical Society, Published in: http://pubs.acs.org/doi/pdf/10.1021.bi960420u.
J. Briggs et al., "Cystatin E/M suppresses legumain activity and invasion of human melanoma", "BMC Cancer", Jan. 2010, pp. 1-13, vol. 10, No. 17, Publisher: BioMed Central Ltd., Published in: http://www.biomedcentral.com/1471-2407/10/17.
Jeanne Brygier et al., "Preparation and Preliminary Characterization of Poly(ethylene glycol)-Pepstatin Conjugate", "Applied Biochemistry and Biotechnology", 1994, pp. 1-10, vol. 47, Publisher: Humana Press.
Chii-Shiarng Chen et al., "Probing the Cathepsin D Using a BODIPY FL-Pepstatin A: Applications in Fluorescence Polzarization and Microscopy", "Journal of Biochemical and Biophysical Methods", 2000, pp. 137-151, vol. 42, No. 3, Publisher: Elsevier Science, Published in: http://www.sciencedirect.com/science/article/pii/S0165022X00000488.
J. Colbert et al., "Diverse regulatory roles for lysosomal proteases in the immune response", "Wiley Online Library", Jul. 2009, pp. 29552965, vol. 39, No. 11, Publisher: European Journal of Immunology, Published in: http://onlinelibrary.wiley.com/doi/10.1002/eji.200939650/full.
Lelia Delamarre et al., "Enhancing immunogenicity by limiting susceptibility to lysosomal proteolysis", "Journal of Experimental Medicine", 2006, pp. 2049-2055, vol. 203, No. 9, Publisher: Rockefeller University Press, Published in: www.jem.org/cgi/doi/10.1084/jem.20052442.
P. Doyle et al., "Drugs Targeting Parasite Lysosomes", "Current Pharmaceutical Design", Mar. 2008, pp. 889-900, vol. 14, No. 9, Publisher: Bentham Science Publishers, Published in: http://www.ingentaconnect.com/content/ben/cpd/2008/00000014/00000009/art0008.
Paul Free et al., "Mannose-pepstatin conjugates as targeted inhibitors of antigen processing", "Organic & Biomolecular Chemistry", 2006, pp. 1817-1830, vol. 4, No. 9, Publisher: Royal Society of Chemistry, Published in: http://pubs.rsc.org/en/Content/ArticleLanding/2006/OB/b6000060f#!divAbstract.

(Continued)

*Primary Examiner* — Nashaat Nashed
(74) *Attorney, Agent, or Firm* — Evans & Molinelli PLLC; Judith A. Evans

(57) ABSTRACT

The present invention relates to a multi-functional protease inhibitor, which may be conjugated to various molecules. The present invention also relates to uses of the protease inhibitor and conjugates thereof.

23 Claims, 22 Drawing Sheets

(56) References Cited

OTHER PUBLICATIONS

Koji Furuno et al., "Receptor-Mediated Introduction of Pepstatin-Asialofetuin Conjugate into Lysosomes of Rat Hepatocytes", "Journal of Biochemistry", 1983, pp. 246-256, vol. 93, No. 1, Publisher: Japanese Biochemical Society, Published in: http://jb.oxfordjournals.org/content/93/1/249.full.pdf+html.

Garth Hamilton et al., "Cystatin F is a cathepsin C-directed protease inhibitor regulated by proteolysis", "The EMBO Journal", 2008, pp. 499-508, vol. 27, No. 3, Publisher: European Molecular Biology Organization, Published in: http://emboj.embopress.org/content/27/3/499.

Y. Henskens et al., "Cystatins in Health and Disease", "PubMed", Feb. 1996, pp. 71-86, vol. 377, No. 2, Publisher: Nat'l Center for Biotechnology Information, Published in: http://www.ncbi.nlm.nih.gov/pubmead/8868064.

Daniel Keppler, "Towards novel anti-cancer strategies based on cystatin function", "Science Direct", Apr. 2006, pp. 159-176, vol. 235, No. 2, Publisher: Elsevier, Published in: http://www.sciencedirect.com/science/article/pii/S0304383505002934.

Donmienne Leung et al., "Protease Inhibitors: Current Status and Future Prospects", "Journal of Medicinal Chemistry", Feb. 10, 2000, pp. 305-341, vol. 43, No. 3, Publisher: American Chemical Society, Published in: http://pubs.acs.org/doi/abs/10.1021.jm990412m?journalCode=jmcmar.

Emmanuelle Liaudet-Coopman et al., "Cathepsin D: newly discovered functions of a long-standing aspartic protease in cancer and apoptosis", "Cancer Letters", 2006, pp. 167-179, vol. 237, No. 2, Publisher: Elsevier, Published in: http://www.elsevier.com/locate/canlet.

Benedicte Manoury et al., "An Asparaginyl Endopeptidase Processes a Microbial Antigen for Class II MHC Presentation", "Nature", 1998, pp. 695-699, vol. 396, No. 6712, Publisher: Macmillan Publishers Ltd, Published in: http://www.nature.com/nature/journal/v396/n6712/pdf/396695a0.pdf.

Stephen P. Matthews et al., "Distinct Protease Requirements for Antigen Presentation In Vitro and In Vivo", "Journal of Immunology", 2010, pp. 2423-2431, vol. 184, No. 5, Publisher: The American Association of Immunologists, Inc., Published in: http://www.jimmunol.org/.

Catherine X. Moss et al., "Destructive potential of the aspartyl protease cathepsin D in MHC class II-restricted antigen processing", "European Journal of Immunology", 2005, pp. 3442-3451, vol. 35, No. 12, Publisher: Wiley-VCH Verlag GmbH & Co., Published in: http://onlinelibrary.wiley.com/doi/10.1002/eji.2002535320/pdf.

G. Nicotra et al., "High Expression of Cathepsin D in Non-Hodgkin's Lymphomas negatively impacts on clincial outcome", "PubMed", 2010, pp. 167-183, vol. 28, No. 3, Publisher: National Center for Biotechnology Information, Published in: http://www.ncbi.nlm.nih.gov/pubmed/20534902.

Hans-Hartwig Otto & Tanja Schirmeister, "Cysteine Proteases and Their Inhibitors", "Chemical Reviews", 1997, pp. 133-172, vol. 97, No. 1, Publisher: ACS Publications, Published in: http://pubs.acs.org/doi/pdf/10.1021/cr950025u.

Carmela Palermo & Johanna A. Joyce, "Cysteine cathepsin proteases as pharmacological targets in cancer", "Trends in Pharmacological Sciences", 2007, pp. 22-28, vol. 29, No. 1, Publisher: Cancer Biology and Genetics Program, Memorial Sloan Kettering Cancer Center, Published in: http://www.sciencedirect.com/science/article/pii/S016561470700274X.

Maximilian Wei-Lin Popp & Hidde L. Ploegh, "Making and Breaking Peptide Bonds: Protein Engineering Using Sortase", "Angewandte Chemie International Edition", 2011, pp. 5024-5032, vol. 50, No. 22, Publisher: Wiley-VCH Verlag GmbH & Co, Published in: http://onlinelibrary.wiley.com/doi/10.1002/anie/201008267/pdf.

Eun-Ang Raiber et al., "Targed Delivery of Antigen Processing Inhibitors to Antigen Presenting Cells Via Mannose Receptors", "ACS Chemical Biology", 2010, pp. 461-476, vol. 5, No. 5, Publisher: American Chemical Society, Published in: http://pubs.acs.org/doi/abs/10.1021/cb100008p.

J. Reiser et al., "Specialized roles for cysteine cathepsins in health and disease", "The Journal of Clinical Investigation", 2010, pp. 3421-3431, vol. 120, No. 10, Publisher: American Society for Clinical Investigation, Published in: http://www.jci.org/articles/view/42918.

Paul G. Richardson et al., "Bortezomib or High-Dose Dexamethasone for Replapsed Multiple Myeloma", "The New Englad Journal of Medicine", 2005, pp. 2487-2498, vol. 352, No. 24, Publisher: Massachusetts Medical Society, Published in: http://www.nejm.org/doi/full/10.1056/NEJMoa043445.

J. Rozman-Pungercar et al., "Inhibition of papain-like cysteine proteases and legumain by caspase-specific inhibitors", "Cell Death and Differentiation", 2003, pp. 881-888, vol. 10, No. 8, Publisher: Nature Publishing Group, Published in: http://www.nature.com/cdd/journal/v10/n8/pdf/4401247a.pdf.

Boris Turk et al., "Lysosomal Cysteine Proteases: More Than Scavengers", "Biochimica et Biophysica Acta BBA", 2000, pp. 98-111, vol. 1477, Publisher: Elsevier, Published in: http://www.sciencedirect.com/science/journal/03044165.

Hamao Umezawa et al., "Pepstain, a New Pepsin Inhibitor Produced by Actinomycetes", "The Journal of Antibiotics", 1970, pp. 259-262, vol. 23, No. 5, Publisher: Antibiotics Research Association, Published in: Tokyo, Japan.

Sander I. Van Kasteren et al., "Site-Selective Glycosylation of Proteins: Creating Synthetic glycoproteins", "Nature Protocols", 2007, pp. 3185-3194, vol. 2, No. 12, Publisher: Nature Publishing Group, Published in: http://www.nature.com/nprot/journal/v2/n12/pdf/nprot.2007.430.pdf.

Nousheen Zaidi et al., "A novel cell penetrating aspartic protease inhibitor blocks processing and presentation of tetanus toxoid . . . ", "Biochemical and Biophysical Research Communications", 2007, pp. 243-249, vol. 364, No. 2, Publisher: Elsevier, Published in: http://www.sciencedirect.com/science/article/pii/S0006291X07021134.

Jeff D. Colbert et al., "Internalization of Exogenous Cystatin F Supresses Cysteine Proteases and Induces the Accumulation of Single-chain . . . ", "Journal of Biological Chemistry", 2011, pp. 42082-42090, vol. 286, No. 49, Publisher: American Society for Biochemistry and Molecular Biology, Published in: http://www.jbc.org/content/286/49/42082.full.pdf+html.

European Patent Office, "International Search Report and Written Opinion for the corresponding PCT application No. GB2012/000660", 2012, pp. 1-5.

Paola Matarrese et al., "Pepstatin A alters host cell autophagic machinery and leads to a decrease in influenza A virus production", "Journal of Cellular Physiology", 2011, pp. 3368-3377, vol. 2226, No. 12, Publisher: Wiley, Published in: http://onlinelibrary.wiley.com/doi/10.1002/jcp.22696/suppinfo.

Sander I. Van Kasteren et al., "A Multifunctional Protease Inhibitor to Regulate Endolysosomal Function", "ACS Chemical Biology", 2011, pp. 1198-1204, vol. 6, No. 11, Publisher: American Chemical Society, Published in: http://pubs.acs.org/doi/pdf/10.1021/cb200292c.

H. Wallin et al., "Cystatins—Extra- and intracellular cysteine protease inhibitors: High-level secretion and uptake of cystatin C in . . . ", "Biochimie", 2010, pp. 1625-1634, vol. 92, No. 11, Publisher: Masson, Published in: http://www.sciencedirect.com/science/article/pii/S030090841000297X.

C. Watts et al., "Asparaginyl endopeptidase: case history of a class II MHC compartment protease", "Immunological Reviews", 2005, pp. 218-228, vol. 207, Publisher: Blackwell Publishing, Published in: Munksgaard.

Colin Watts, "The endosome lysosome pathway and information generation in the immune system", "Biochimica et Biophysica Acta (BBA)—Proteins and Proteomics", 2011, pp. 1421, vol. 1824, No. 1, Publisher: Elsevier, Published in: http://www.sciencedirect.com/science/article/pii/S1570963911002019.

\* cited by examiner

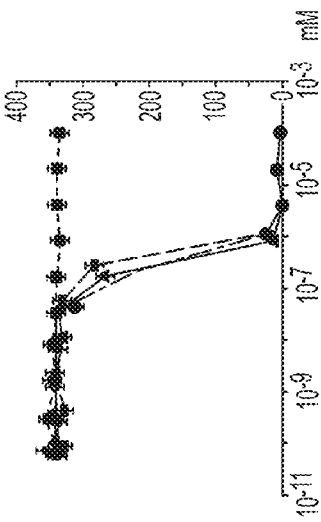
FIG. 8A
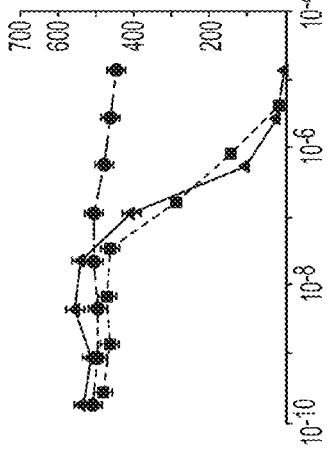
FIG. 8B
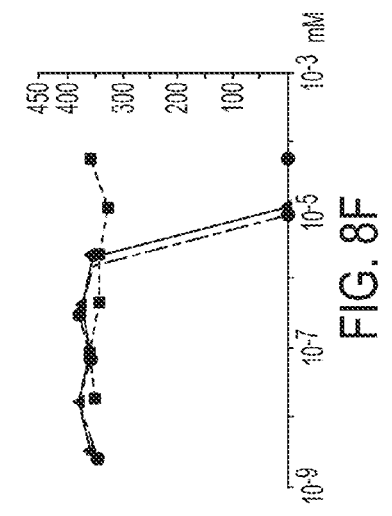
FIG. 8C
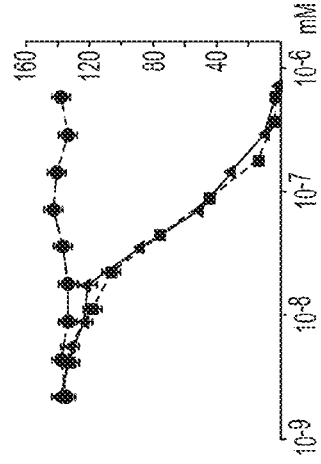
FIG. 8D
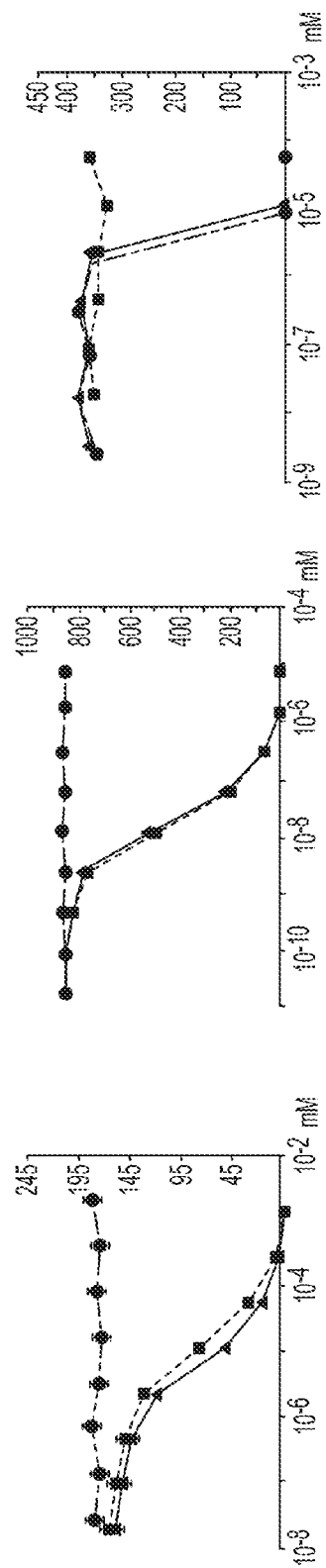
FIG. 8E
FIG. 8F

SEQUENCE LISTING

<160> NUMBER OF SEQ ID NOS: 8

<210> SEQ ID NO 1
<211> LENGTH: 32
<212> TYPE: DNA
<213> ORGANISM: Artificial Sequence
<220> FEATURE:
<223> OTHER INFORMATION: primer sequence

<400> SEQUENCE: 1
caggattaca attggtacca tggccgggcc cc                        32

<210> SEQ ID NO 2
<211> LENGTH: 43
<212> TYPE: DNA
<213> ORGANISM: Artificial Sequence
<220> FEATURE:
<223> OTHER INFORMATION: primer sequence

<400> SEQUENCE: 2
gcctactcga gcttaatgat gatgatgatg atggtcctga cag               43

<210> SEQ ID NO 3
<211> LENGTH: 29
<212> TYPE: DNA
<213> ORGANISM: Artificial Sequence
<220> FEATURE:
<223> OTHER INFORMATION: primer sequence

<400> SEQUENCE: 3
caggtgtacc aagtgccagc ccaacttgg                            29

<210> SEQ ID NO 4
<211> LENGTH: 29
<212> TYPE: DNA
<213> ORGANISM: Artificial Sequence
<220> FEATURE:
<223> OTHER INFORMATION: primer sequence

<400> SEQUENCE: 4
ccaagttggg ctggcacttg gtacacgtg                            29

<210> SEQ ID NO 5
<211> LENGTH: 10
<212> TYPE: PRT
<213> ORGANISM: Artificial Sequence
<220> FEATURE:
<223> OTHER INFORMATION: linker peptide

<400> SEQUENCE: 5

Gly Asp Ser Asp Ser Asp Ser Asp Ser Gly
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide

<400> SEQUENCE: 6

Gly Lys Asp Asp Asp Asp Lys Tyr Asp Gly
1               5                   10

```
<210> SEQ ID NO 7
<211> LENGTH: 12
<212> TYPE: PRT
<213> ORGANISM: Artificial Sequences
<220> FEATURE:
<223> OTHER INFORMATION: Synthetic peptide

<400> SEQUENCE: 7

Gly Lys Gly Asp Ser Asp Ser Asp Ser Asp Ser Gly
1               5                   10

<210> SEQ ID NO 8
<211> LENGTH: 146
<212> TYPE: PRT
<213> ORGANISM: Homo sapiens
<220> FEATURE:
<221> NAME/KEY: misc_feature
<223> OTHER INFORMATION: Cystatin C

<400> SEQUENCE: 8

Met Ala Gly Pro Leu Arg Ala Pro Leu Leu Leu Leu Ala Ile Leu Ala
1               5                   10                  15

Val Ala Leu Ala Val Ser Pro Ala Ala Gly Ser Ser Pro Gly Lys Pro
            20                  25                  30

Pro Arg Leu Val Gly Gly Pro Met Asp Ala Ser Val Glu Glu Glu Gly
        35                  40                  45

Val Arg Arg Ala Leu Asp Phe Ala Val Gly Glu Tyr Asn Lys Ala Ser
    50                  55                  60

Asn Asp Met Tyr His Ser Arg Ala Leu Gln Val Val Arg Ala Arg Lys
65                  70                  75                  80

Gln Ile Val Ala Gly Val Asn Tyr Phe Leu Asp Val Glu Leu Gly Arg
                85                  90                  95

Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
        115                 120                 125

Ala Val Pro Trp Gln Gly Thr Met Thr Leu Ser Lys Ser Thr Cys Gln
    130                 135                 140

Asp Ala
145
```

INHIBITORS AGAINST ENDOSOMAL/LYSOSOMAL ENZYMES

CROSS-REFERENCE TO RELATED APPLICATIONS

This application is a 371 national stage application of PCT Application No. PCT/GB2012/000660, filed Aug. 15, 2012, and claims the benefit of United Kingdom Application No. GB1114017.5, filed on Aug. 15, 2011, the entire contents of which are hereby incorporated by reference as if fully set forth herein.

FIELD OF THE INVENTION

The present invention relates to a multi-functional protease inhibitor, which may be conjugated to various molecules. The present invention also relates to uses of the protease inhibitor and conjugates thereof.

BACKGROUND TO THE INVENTION

Protease inhibitors have emerged as a powerful drug class[1]. They include the inhibitors of angiotensin converting enzyme, inhibitors of HIV proteases and proteasomal inhibitors such as Bortezomib (Velcade) used to treat multiple myeloma[2].

The proteases of the endo-lysosomal pathway have frequently been proposed as therapeutic targets as they play important roles in the regulation of a wide variety of biological systems[3]. For example, lysosomal cysteine and aspartyl proteases are validated drug targets in several trypanosome species[4] and the upregulation of certain endosomal proteases is associated with increased malignancy[5]. Asparagine endopeptidase (AEP or legumain) has also been implicated in the progression of malignant melanoma[6], in the destruction of the therapeutic drug 1-asparaginase and in neuroexitotoxicity[7]. Down-regulation of cystatins, which are natural cysteine protease inhibitors, can lead to increased malignancy[8] and faulty immune responses[9]. High expression of Cathepsin D (Cat D) in non-Hodgkin's lymphoma has also been associated with increased malignancy[10] and is also associated with poor prognosis in breast cancer[11]. A further potential therapeutic application of endosomal protease inhibitors would be immune modulation since several recent studies demonstrate that the proteolytic activity in endosomes of antigen presenting cells may be too high leading to antigen destruction and inefficient presentation to T-cells. Consequently, protease resistant antigens often elicit more robust immune responses[12,13].

Taken together, it seems that effective down-modulators of endo/lysosomal protease activity could be a valuable addition to the therapeutic armoury. However, to date modulation of endo/lysosomal protease function has remained challenging, as there are multiple families of endosomal proteases with an extensive functional redundancy[14]. As an additional problem, there is evidence in the literature that the knock-down/inhibition of specific proteases leads to the upregulation of others[3,15].

Most endosomal proteases belong to 3 distinct families: There are several papain-like cysteine proteases (PLCPs), including cathepsin L,S,B,C and several others[16]. Alongside these there are the aspartyl proteases related to pepsin; cathepsins D and E. Finally, there is an additional cysteine protease termed asparaginyl endopeptidase (AEP) or legumain which is more closely related to the caspases[17]. Each of these 3 classes can be inhibited by distinct and non-overlapping small molecule inhibitors[18], but in vivo inhibition, or knock-out, of these proteases frequently shows limited or no phenotype most likely due to functional redundancy. We thus postulated that inhibiting all three families of endosomal proteases in an endosome-specific manner would provide a powerful tool for modulating endo/lysosomal function.

PLCPs and AEP are potently inhibited by a naturally occurring 14 kDa protein, cystatin C. The cystatins are a family of small proteins, that inhibit PLCPs with sub-nanomolar affinity[19]. They are present in the bloodstream and are believed to play a role in the mopping up of proteases released during physiological and pathological responses. Importantly cystatin C, as well as several family members, inhibit AEP via a distinct binding site with a Ki of 0.20 nM[20] (FIG. 1). Cystatin C thus represents an excellent scaffold for the synthesis of a pan-endosomal protease inhibitor.

Cathepsin D and E, the endosomal aspartyl proteases are inhibited with a Ki of 0.1 nM by pepstatin A[21], an isopeptide first isolated from *Actinomyces*. Its major drawback is its virtual insolubility in aqueous media[21]. Nonetheless it is still widely used even in cell based assays because more soluble alternatives are not readily available. Several attempts have been made to address this problem, such as conjugating pepstatin A to asialoglycoprotein(ASGP)[22], or to poly(ethylene glycol)[23], or more recently to directly mannosylate it, or conjugate it to mannosylated bovine serum albumin[24]. PEGylation of Pepstatin reduces its inhibitory potential 400-fold, and conjugating to mannosylated BSA-reduces the Ki 10-fold, whereas conjugation to ASGP renders pepstatin inactive until the protein backbone is digested. Conjugation of pepstatin to peptides or fluorescent moieties did not significantly alter its inhibitory potential[25].

SUMMARY OF THE INVENTION

The present invention is based in part on the provision of a cysteine protease inhibitor/aspartyl protease inhibitor conjugate, which displays multi-functional protease inhibition activity.

Thus, in a first aspect there is provided a multi-functional protease inhibitor comprising a cystatin/pepstatin A conjugate.

The present inventors have observed that it is possible through conjugating pepstatin A (which on its own is very insoluble) to a cystatin, such as cystatin C, to form a highly water-soluble molecule. Moreover, such a conjugate displays inhibitory activity against at least two of the following classes of proteases: cysteine proteinases, aspartyl proteinases; and/or asparaginyl endopeptidases (AEP).

It will be appreciated that various physiologically acceptable salts, solvates, esters, amides or other physiologically functional derivative thereof of the conjugates described herein, may also be suitable and the skilled addressee is aware how such molecules may be prepared.

Thus, the term multi-functional is understood to mean that the conjugates of the present invention have an inhibitory activity against at least two enzymatically distinct proteases, such as at one cysteine proteinase, and one aspartyl proteinase and/or asparaginyl endopeptidase, with inhibitory constants of smaller than 10 μM. The cystatins have evolved to inhibit multiple cysteine proteases thus while only one protease molecule (and one AEP) can be engaged at any one time, they are broadly suppressive of this class of proteases.

Advantageously, the present inventors have been able to provide conjugates which are significantly soluble in aqueous solution with solubility greater than 50 nM, but typically greater than 500 nM, such as in the order of 1 μM in aqueous buffer in the pH range of 3-10, such as 4-8, or water itself. This may be achieved by incorporation of a peptide moiety between the cystatin molecule and pepstatin A. Typically any solubilising peptide may be 2 to 30 amino acids in length and should be sufficiently hydrophilic to solubilise hydrophobic inhibitor components. As well as facilitating solubilisation, the peptide may also allow for the conjugate to be targeted to desired tissues, cells and the like. In this manner the peptide itself may conventionally be a targeting peptide known in the art, or the peptide may be capable, through further modification, of incorporating one or more targeting moieties. Typically, the peptide moiety is >4 amino acid residues long and contains at least 2 amino acids with side chains that possess charges at neutral pH, and/or have hydrophilic and/or polar side chains. Preferably the peptide may comprise one or more amino acid residues that do not affect the ability of the conjugate to inhibit proteases, for example amino acids that possess negative charges at neutral pH, or those possessing hydroxyl or carboxylic acid side chains.

Unnatural amino acids, for example those that carry azido or alkyne functionality in their side chain may be employed, such as those that can be further modified by additional chemical or enzymatic reactions, for example by copper-catalyzed Huisgen cyclo-addition reactions or using sortase enzymes[26]. Reactive side chains on the peptides and/or modified residues may facilitate co-conjugation of the inhibitor to another moiety, such as a targeting protein, thereby facilitating the delivery to specific cell types and tissues (see text and FIG. 18, for example, for further details).

A specific example of a solubilising tag is the FLAG-tag[27], but other peptides can be used.

Typically, conjugation of cystatin to pepstatin A may be through a cysteine present on the cystatin molecule, or the cystatin may be modified, through mutagenesis techniques known to the skilled addressee, in order to introduce a cysteine moiety which is capable of facilitating conjugation to pepstatin A, optionally via a solubilising peptide. Modification through lysines, or through unnatural amino acids introduced by methods known to the skilled addressee are also possible[28]. The skilled addressee is able to determine which residues may be appropriate whilst ensuring that protease inhibitory activity of the cystatin molecule will remain substantially unchanged, by biochemical means, or by comparing sequence analogies to known cystatins, or by determining location of the inhibitory motifs and of the chosen residues in a protein X-ray crystal structure. In a preferred embodiment, the cystatin is cystatin C and a preferred residue to allow conjugation of pepstatin A is threonine 102, or arginine 77, or Leucine 117, as numbered according to GenBank: CAA36497.1 (SEQ. ID. NO: 8), which may be replaced with a cysteine residue, which is subsequently capable of reaction, so as to allow conjugation to pepstatin A, preferably via a solubilising peptide. Modification of the identified residue may be carried out, through site directed mutagenesis, for example, in order to replace the residue with a more reactive residue, such as a cysteine or azidohomoalanine, which allows conjugation to pepstatin A.

Also mutants and other cystatin family inhibitors can also be used that have different inhibitory profiles for the different proteases. For example binding regions of cystatin C can be mutated so that the inhibition of specific proteases or families is reduced or altered[29]. Further, the latent cystatin, cystatin F can also be used whose PLCP reactivity is only revealed (by dimer to monomer conversion) following uptake into cells[30].

In a second aspect the present invention provides a pharmaceutical composition comprising a protease inhibitor conjugate molecule of the present invention, together with a pharmaceutically acceptable carrier therefore.

Viewed from a third aspect, the invention provides a conjugate or formulation of the first or second aspect, or physiologically acceptable salt, solvate, ester, amide or other physiologically functional derivative thereof, for use in medicine.

Viewed from a further aspect, the invention provides a conjugate of the invention, or physiologically acceptable salt, solvate, ester, amide or other physiologically functional derivative thereof, for the treatment or prophylaxis of a disease, particularly where it is desirable to inhibit proteases which may be associated with a particular disease or where there inhibition may facilitate the treatment of a disease. Such diseases may include cancer, inflammatory disease, autoimmune diseases, parasitic disease e.g Trypanosomiasis and relevant lysosomal storage diseases, such as galactosialidosis, Gaucher's disease[3], and others.

Viewed from a further aspect, the invention provides a method of treatment or prophylaxis of a disease/condition associated with protease expression and/or function said method comprising administering a therapeutically or prophylactically useful amount of a conjugate of the invention, or physiologically acceptable salt, solvate, ester, amide or other physiologically functional derivative thereof, or a pharmaceutical formulation of the present invention, to a subject in need thereof.

Viewed from a further aspect, the invention provides use of a conjugate of the invention, or physiologically acceptable salt, solvate, ester, amide or other physiologically functional derivative thereof, in the manufacture of a medicament for use in any treatment or prophylaxis as defined herein.

Viewed from a further aspect the conjugates/inhibitors of the invention may be used to enhance the performance of vaccines specifically by attenuating their known tendency to be unproductively or destructively processed (references 12 & 13). Thus the conjugates of the invention may also be administered in conjunction with other agents, such as other therapeutic agents or may be a component of a vaccine and administered in conjunction with immunogenic agents. Examples of such other therapeutic agents include subunit or peptide vaccines with appropriate adjuvants, such as solid phase or emulsion carriers, immune system adjuvants and other agents to improve the vaccine response. The conjugate can also be added to live cell vaccines for the aim of improving the efficacy thereof. For the case of active conjugates combined with other therapies the two or more treatments may be given individually varying dose schedules and/or via different routes. Admixtures of the conjugate and vaccine protein optionally also with adjuvant can be co-encapsulated for example in PLGA microspheres, liposomes or other carriers for delivery purposes.

In a further aspect, taking advantage of the inhibitor's demonstrated ability to boost growth factor receptor signalling and attenuate the down-regulation of the same (see FIG. 10(A)-10(B)-11(A)-11(C)), the inhibitor when administered topically in combination with growth factors, such as, but not limited to EGF, may aid the natural process of wound healing.

The combination of a therapeutic or prophylactic agent with a conjugate of the present invention would be at the discretion of the physician who would select dosages using his common general knowledge and dosing regimens known to a skilled practitioner.

Where a conjugate of the invention is administered in combination therapy with one, two, three, four or more, preferably one or two, preferably one other therapeutic/prophylactic agents, the components can be administered simultaneously or sequentially. When administered sequentially, they can be administered at closely spaced intervals (for example over a period of 5-10 minutes) or at longer intervals (for example 1, 2, 3, 4 or more hours apart, or even longer period apart where required), the precise dosage regimen being commensurate with the properties of the therapeutic agent(s).

The patient is typically an animal, e.g. a mammal, especially a human.

By a therapeutically or prophylactically effective amount is meant one capable of achieving the desired response, and will be adjudged, typically, by a medical practitioner. The amount required will depend upon one or more of at least the active conjugate(s) concerned, the patient, the condition it is desired to treat or prevent and the formulation of order of from 1 μg to 1 g of conjugate per kg of body weight of the patient being treated.

Different dosing regiments may likewise be administered, again typically at the discretion of the medical practitioner. As alluded to hereinafter the low toxicity of the compounds of the invention and their targetability to specific cell types, allow for at least daily administration although regimes where the compound(s) is (or are) administered more infrequently, e.g. every other day, weekly or fortnightly, for example, are also embraced by the present invention.

By treatment is meant herein at least an amelioration of a condition suffered by a patient; the treatment need not be curative (i.e. resulting in obviation of the condition). Analogously references herein to prevention or prophylaxis herein do not indicate or require complete prevention of a condition; its manifestation may instead be reduced or delayed via prophylaxis or prevention according to the present invention.

For use according to the present invention, the conjugates or physiologically acceptable salt, solvate, ester or other physiologically acceptable functional derivative thereof described herein may be presented as a pharmaceutical formulation, comprising the conjugate or physiologically acceptable salt, ester or other physiologically functional derivative thereof, together with one or more pharmaceutically acceptable carriers therefor and optionally other therapeutic and/or prophylactic ingredients. Any carrier(s) are acceptable in the sense of being compatible with the other ingredients of the formulation and not deleterious to the recipient thereof.

Examples of physiologically acceptable salts of the conjugates according to the invention include acid addition salts formed with organic carboxylic acids such as acetic, lactic, tartaric, maleic, citric, pyruvic, oxalic, fumaric, oxaloacetic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

Physiologically functional derivatives of compounds of the present invention are derivatives, which can be converted in the body into the parent conjugate. Such physiologically functional derivatives may also be referred to as "pro-drugs" or "bioprecursors". Physiologically functional derivatives of conjugates of the present invention include hydrolysable esters or amides, particularly esters, in vivo. Determination of suitable physiologically acceptable esters and amides is well within the skills of those skilled in the art.

It may be convenient or desirable to prepare, purify, and/or handle a corresponding solvate of the conjugates described herein, which may be used in the any one of the uses/methods described. The term solvate is used herein to refer to a complex of solute, such as a compound or salt of the compound, and a solvent. If the solvent is water, the solvate may be termed a hydrate, for example a mono-hydrate, di-hydrate, tri-hydrate etc, depending on the number of water molecules present per molecule of substrate.

It will be appreciated that the conjugates of the present invention may exist in various stereoisomeric forms and the compounds of the present invention as hereinbefore defined include all stereoisomeric forms and mixtures thereof, including enantiomers and racemic mixtures. The present invention includes within its scope the use of any such stereoisomeric form or mixture of stereoisomers.

The conjugates of the present invention may be prepared using reagents and techniques readily available in the art and/or exemplary methods as described hereinafter.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. Methods typically include the step of bringing into association an active conjugate with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active conjugate with an inert liquid diluent. Tablets may be optionally coated and, if uncoated, may optionally be scored. Capsules may be prepared by filling an active conjugate, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active conjugate is formulated in an appropriate release-controlling matrix, or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active conjugate with the softened or melted carrier(s) followed by chilling and shaping in moulds.

Pharmaceutical formulations suitable for parenteral administration include sterile solutions or suspensions of an active conjugate in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active conjugate may be in powder form which is constituted with a suitable vehicle, such as sterile, pyrogen-free water, before use.

An active conjugate may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active conjugate is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microliters, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active conjugate in aqueous or oily solution or suspension.

It should be understood that in addition to the aforementioned carrier ingredients the pharmaceutical formulations described above may include, an appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutically acceptable carriers are well known to those skilled in the art and include, but are not limited to, 0.1 M and preferably 0.05 M phosphate buffer or 0.8% saline. Additionally, pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

Therapeutic formulations for veterinary use may conveniently be in either powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w and preferably 60 to 80% w/w of the active ingredient(s) and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain the conjugate or a derivative or salt thereof and may optionally include a veterinarily acceptable water-miscible solvent, for example polyethylene glycol, propylene glycol, glycerol, glycerol formal or such a solvent mixed with up to 30% v/v of ethanol. The liquid concentrates may be administered to the drinking water of animals.

BRIEF DESCRIPTION OF THE DRAWINGS

The present invention will now be further described with reference to the following figures which show.

MATERIALS AND METHODS

Figure 1:
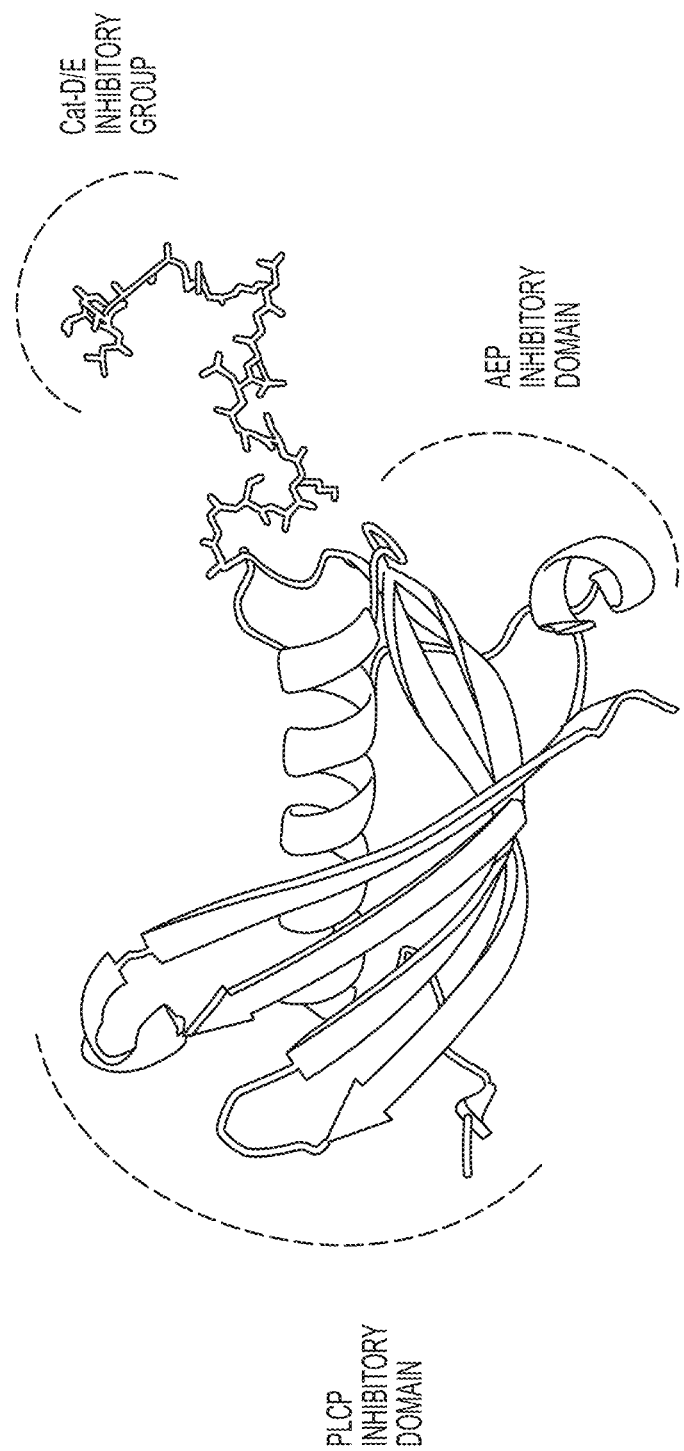
FIG. 1 is a representation of a cystatin-pepstatin conjugate as a potential inhibitor (CPI) of all 3 major endosomal protease families: the papain-like cysteine proteases (PLCP), aspartyl proteases (Cat-D/E) and asparagine endopeptidase.

Ovalbumin was purchased from Sigma-Aldrich (A5503), or Worthingtons (LS3056; In vitro digest), Cystatin C from Genway (11-511-248839). Bovine serum albumin and Myoglobin (from horse-heart) were purchased from Sigma-Aldrich. anti-Ovalbumin was obtained from Polysciences (2344-5) Anti-5His was purchased from Quiagen (34660), anti-Cystatin C (mAb1196) and recombinant cathepsins came from R&D systems. Pepstatin A and fluorescent substrates were purchased from Bachem. NBoc-1-Cysteine Methanethiosulfonate was purchased from Toronto Research Chemicals (B646250).

Cloning and Expression of Cystatin C-T102C-6His Mutant

The Cystatin C was amplified as described previously[1] using the following primers: CysCFor (caggattacaattggtaccatggccgggcccc) (SEQ. ID. NO: 1) and CysCRev (gcctactcgagcttaatgatgatgatgatgatggtcctgacag) (SEQ. ID. NO: 2) to introduce a C-terminal 6-Histidine tag. The amplification product was cloned into a pcDNA-DHFR vector used previously between XhoI and KpnI restriction sites.

Threonine 102 was determined to be solvent accessible using the NAccess software[3] based on the crystal structure of human Cystatin C[4] and domain-swapped human Cystatin C[5]. It was also a residue away from the inhibitory motifs of both the papain-like Cathepsins and asparagine endopeptidase[6].

The Mutations were introduced with primers CysCT102Cfor (caggtgtaccaagtgccagcccaacttgg) (SEQ. ID. NO: 3) and CysCT102Crev (ccaagttgggctggcacttggtacacgtg) (SEQ. ID. NO: 4).

DHFR-negative CHO cells were grown in DMEM-based medium containing 10% dialysed FCS, 5 mM Glutamine and 0.1 mM hypoxanthine and 0.01 mM thymidine. Following transfection using lipofectamine with DHFR-CysC-T102C-6His plasmid, the hypoxanthine and thymidine supplement were removed and the cells were cultured at low density in 15 cm dishes (104 cells per dish) in medium containing 20 nM methotrexate (MTX). After 2 days the medium was replaced by medium containing 50 mM MTX. The cells were grown at 5% $CO_2$ at 37° C. for a further 2 days upon which single colonies had begun to form. These were picked and placed in a 96-well plate (tissue culture treated) in medium containing 100 nM methotrexate.

The colonies were assessed for Cystatin C expression levels using an anti-Cystatin C antibody MAB1196 (R&D Systems, mouse anti-Human CysC; 1:3000 dilutions) and the highest producing clones were harvested and transferred to a 24-well dish. Here they were allowed to grow to 80% confluency prior to the addition of medium containing increasing amounts of MTX (up to 2 mM). At the final MTX-concentration one clone (SvKD2-25-A7) was selected for large-scale production of Cystatin C.

This clone was grown to confluency in 10 225 cm$^2$ tissue culture flasks in medium containing 2 mM MTX. The cells were incubated at 37 degrees for 2 weeks prior to harvest of the supernatant. The pH of the supernatant (2 L) was adjusted to 8.0 and NaCl was added to a final concentration of 250 mM. The supernatant was filtered through a 0.22 µm filter prior to passing it over 6 mL of NiNTA agarose (Quiagen) at 4° C. The resin was washed with 10 column volumes of 50 mM $NaPO_4$, 300 mM NaCl (pH 8.3) and 5 column volumes of the same buffer containing 5 mM imidazole. The bound protein was eluted by gently shaking the agarose with 2×8 mL of 500 mM imidazole containing buffer followed by elution.

The eluent was passed over a Superdex G75 column (GE Healthcare, XK26/60) in batches of 1.5 mL. The fractions containing pure Cystatin C were pooled and concentrated by ultrafiltration (MWCO 6-8000) to yield 21 mL of a 0.8 mg/mL protein solution (as determined by UV absorbance). Mass spectrometry (after reduction):

Extended Synthetic Scheme

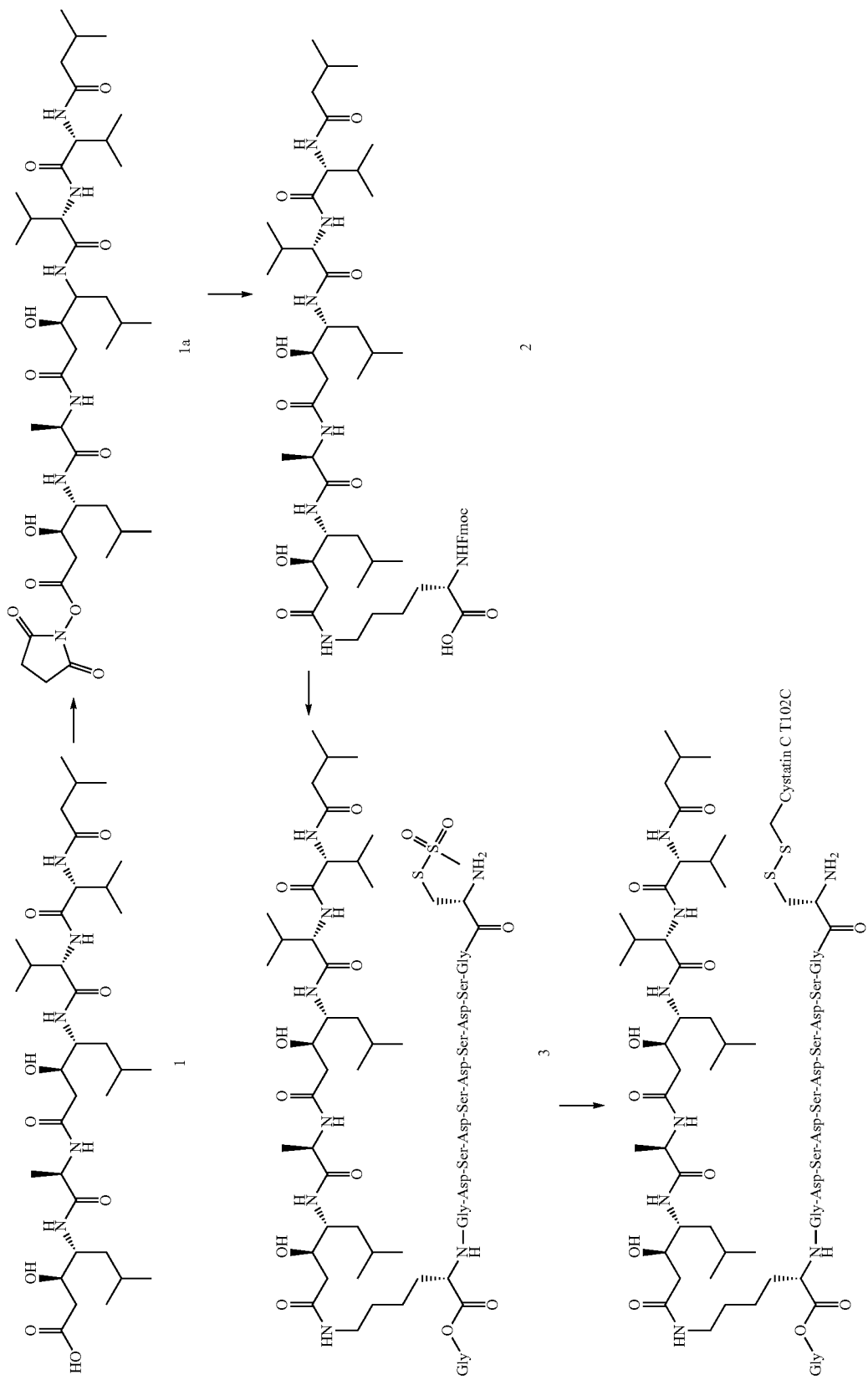

Pepstatin A-N-Hydroxysuccinimidyl Ester (1a)

Pepstatin (147 mg, 0.21 mmol) was dissolved in DMF (15 mL). N-Hydroxysuccinimide (217 mg, 1.4 mmol) and 1-Ethyl-3-(3-dimethylaminopropyl)carbodiimide (323 mg, 1.7 mmol) were added and the mixture was stirred at room temperature for 23 hours. The mixture was concentrated under high vacuum to yield a glass-like solid, which was washed with water (3×15 mL) and diethyl ether (3×15 mL) to yield a white powder (153 mg, 93% yield) of Pepstatin A-N-hydroxysuccinimidyl ester. m/z (ESI+) observed 783.4; calculated: 783.5; 1H NMR (300 MHz, DMSO) δ 7.91 (d, J=7.3 Hz, 1H, NH), 7.80 (dd, J=11.3, 9.0 Hz, 2H, 2×NH), 7.46 (t, J=9.2 Hz, 2H 2×NH), 5.27 (d, J=5.8 Hz, 1H, OH), 4.82 (d, J=5.0 Hz, 1H, OH), 4.33-4.07 (m, 3H), 3.83-3.94 (m, 4H), 2.80 (s, 4H, HOSu), 2.71 (dd, J=16.5, 2.2 Hz, 2H), 2.21-1.84 (m, 5H), 1.67-1.46 (m, 2H), 1.47-1.23 (m, 4H), 1.19 (d, J=7.1 Hz, 3H, CH3), 0.97-0.72 (m, 30H, 10×CH3). 13C NMR (75 MHz, DMSO) δ 172.34, 171.54, 171.09, 170.72, 170.64, 170.05, 167.38, 68.96, 68.37, 57.95, 57.80, 50.64, 50.53, 48.26, 44.38, 40.36, 40.08, 39.80, 39.52, 39.24, 38.96, 38.68, 38.49, 35.27, 30.28, 30.03, 25.62, 25.39, 24.16, 23.37, 23.24, 22.22, 21.76, 21.62, 19.26, 19.22, 18.31, 18.27, 18.09.

Pepstatin A-Lysine (2)

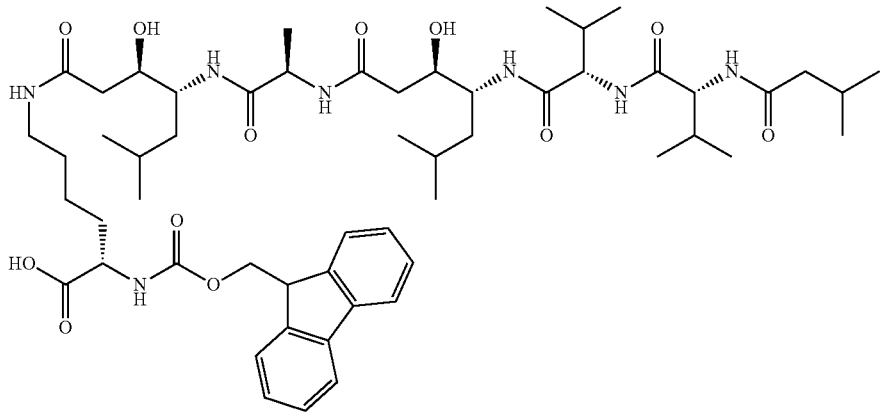 [SMILES: CC(C)CC(=O)N[C@@H](C(=O)N[C@H](C(=O)N[C@H](CC(C)C)[C@H](O)CC(=O)N[C@H](C)C(=O)N[C@H](CC(C)C)[C@H](O)CC(=O)NCCCC[C@H](NC(=O)OCC1c2ccccc2-c2ccccc21)C(=O)O)C(C)C)C(C)C]

30

Pepstatin (164 mg, 0.21 mmol) was dissolved in DMF (20 mL). FMoc-Lysine 77.2 mg, 0.21 mmol) was added and shaken for 2 days at room temperature. The reaction mixture was concentrated under vacuum and washed with 0.1 M HCl solution (2×2×50 mL) and water (6×50 mL) before being lyophilised to yield 148 mg of a white solid, which could be further purified by HPLC. m/z (ESI+) observed: 1036.6; calculated 1036.6. 1H NMR (300 MHz, DMSO) δ 7.91-7.29 (m, 15H, 7×NH & Ar—H), 4.84 (s, 2H, 2×OH), 4.33-4.05 (m, 6H), 3.98-3.67 (m, 5H), 3.02 (dt, J=11.8, 6.5 Hz, 2H), 2.20-1.81 (m, 9H), 1.77-1.22 (m, 15H), 1.20 (d, J=7.0 Hz, 3H), 0.95-0.66 (m, 30H, 10×CH3). 13C NMR (75 MHz, DMSO) δ 173.92, 172.14, 171.54, 171.07, 170.82, 170.67, 170.62, 156.11, 143.81, 143.77, 140.67, 127.60, 127.03, 125.24, 120.06, 69.15, 69.01, 65.57, 57.96, 57.78, 53.74, 50.71, 50.42, 48.33, 46.63, 44.38, 40.35, 40.07, 30.41, 30.28, 30.05, 28.68, 25.62, 24.14, 23.40, 23.22, 23.05, 22.21, 21.89, 21.61, 19.26, 19.21, 18.34, 18.26, 18.13.

Pepstatin-Lys-Peptides-MTS (3)

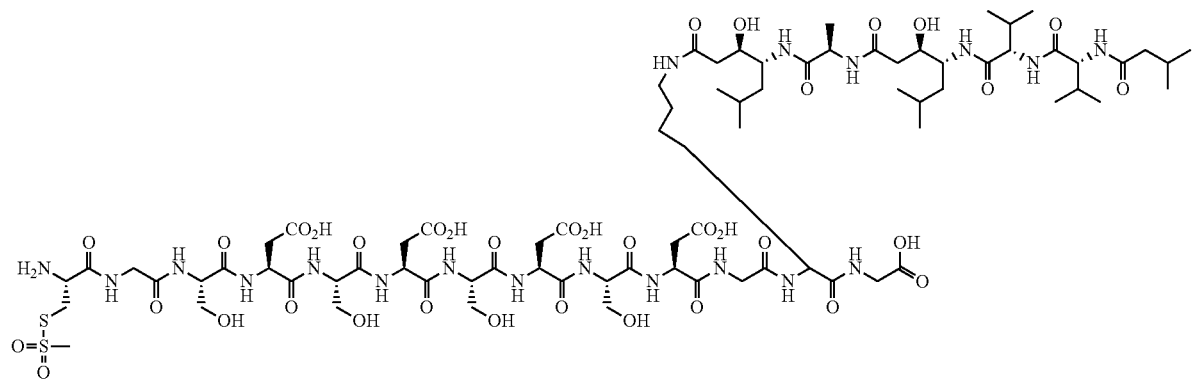

3 was synthesised by standard Fmoc-solid phase peptide chemistry using Pybop as a coupling agent on a Syro I peptide synthesiser. The coupling of Pepstatin-Lysine-Fmoc was reacted for 24 hours. -Boc-Cysteine MTS (TRC Research Chemicals) was introduced manually using standard Pybop coupling conditions in the last step of the synthesis (4-fold excess of amino acid and coupling reagent). m/z (ESI+) observed: 1036.6; calculated 1036.6

Synthesis of the Cystatin-Pepstatin Conjugate (4)

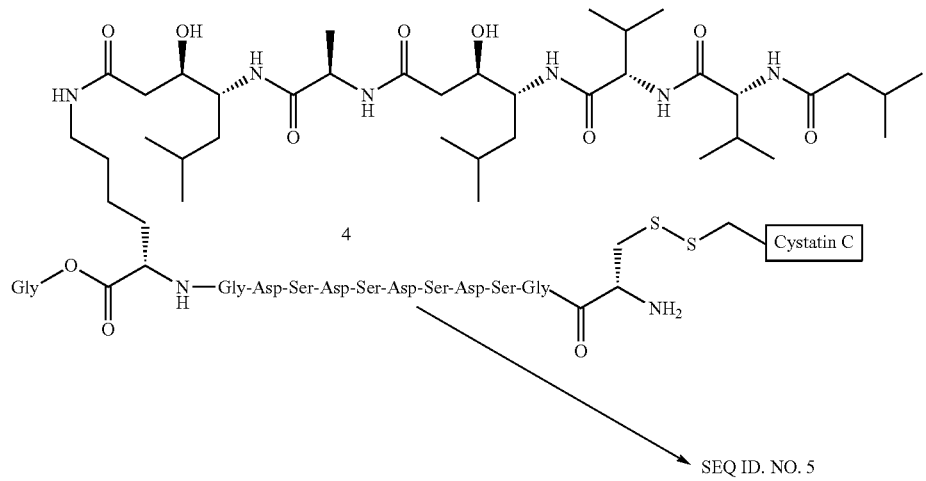

Three further conjugates 5, 6 and 7 were made in a similar fashion, showing that a variety of peptide linker moieties are suitable.

DTT was added to a solution of Cystatin C-T102C-6His (1 mg/mL in PBS, 2.5 mL) to a final concentration of 20 mM. The mixture was gently shaken at room temperature for 15 minutes and buffer exchanged into phosphate buffer (pH 8.5, 100 mM Phosphate, 300 mM NaCl) by Sephadex G-25 resin (GE Healthcare). To the reduced protein (50 µM 3.5 mL) was added a solution of 3 in DMSO (2 mM, 4×50 µL) in 4 portions at 1 hour intervals. Prior to characterization, the modified protein was purified by 6His-affinity chromatography, followed by dialysis (PBS, 6000-8000 MWCO, 3×4 L).

Protease Inhibition Studies

All protease inhibition studies were carried out as described previously[7-9] on a FLUOstar Optima Fluorimeter (BMG) with 360 nm excitation and 460 nm emission wavelength filters as described previously.[1-2,9-10] Recombinant Cathepsin D and Cathepsin S were purchased from R&D Systems. Recombinant Asparagine Endopeptidase was expressed and activated as described previously.[2]

Inhibition of Asparagine Endopeptidase (AEP)

To a AEP (100 ng/well) in assay buffer (50 mM NaOAc, 300 mM NaCL, pH 4.5, 50 µL) was added 10 µL of the inhibitors (in PBS). The plate was then incubated at room temperature for 20 minutes. ZAla-Ala-Asp-MEC was then added (100 µM, Bachem, 60 µL) and 7-amino-4-methylcoumarin release was measured by fluorescence spectroscopy over time. Initial rates were plotted against inhibitor concentration.[10]

Inhibition Studies of Cathepsin D Activity

Cathepsin D inhibition studies were performed as previously described[9].

Inhibition Studies of Cathepsin L

To a solution of activated mouse Cathepsin L (R&D systems, 0.25 ng/µL) in assay buffer (25 mM MES, pH 5.5, 30 µL) were added various serial dilutions of Cystatin C (from 1.4 µM), Cystatin-Pepstatin and Pepstatin alone. The mixture was gently shaken at room temperature for 5 minutes prior to the addition of Z-Leu-Arg-AMC (40 µM in assay buffer, made from a 1 mM DMSO Stock solution). 7-amino-4-methylcoumarin release was measured by fluorescence spectroscopy over time. Initial rates were plotted against inhibitor concentration[11].

Inhibition of Proteases in Dendritic Cell or T. brucei Lysates

Three spleens from C57/B-6 mice or from $10^9$ T. brucei promastigotes were homogenised in a glass homogeniser in 16 mL of citrate buffer (200 mM, pH 5.5). The cells were lysed by repeated freeze/thaw cycles (6 cycles). The supernatant was cleared by centrifugation at 18,000 g for 30 minutes. The cleared supernatant had a protein concentration of 5 mg/mL. 20 µg of lysate was used as protease source in the same inhibition assays as for the recombinant proteases.

Inhibition of Endo-Lysosomal Protease Activity in Live Bone-Marrow Derived Dendritic Cells To a suspension of dendritic cells, derived from bone marrow precursors as described previously[12], (107 Cells, 100 µL) the inhibitors were added (70 µM; 100 µL in PBS). The cells were incubated at 37° C., 5% CO2, for 3 hours. 1 mL of cold cRPMI with 10% FCS was added to each tube and the cells were collected by centrifugation. The cells were washed 3 times with medium prior to lysis (50 µL; 50 mM Citrate, 1% Triton X-100, pH 5.0). 5 µg of this protein mixture was used to determine residual proteolytic activity as described previously[1].

Test of Enzcheck Substrate Using Purified Macrophage Lysosomes

Lysosomes isolated from bone-marrow derived macrophages using a Percoll density-gradient fractionation (400 ng/µL, 10 µL) were resuspended in assay buffer (100 mM Citrate, 2 mM DTT, pH 4.5, 0.5% v/v triton X-100; 590 µL). 50 µL of this diluted lysosomal suspension was plated in triplicates in a 96-well flat-bottomed plate. 10 µL of either cystatin, pepstatin of CPI (3 µM final concentration) was added to each set of three wells with PBS as a control. The mixtures were incubated at room temperature for 20 minutes prior to the addition of EnzChek substrate (Invitrogen, catalog number E6638, 20 µg/mL in assay buffer). Fluorescence emergence (excitation 485 nm; emission 530 nm) was measured every 5 minutes on a fluorescent plate reader at 37° C. Initial rates of fluorescence emergence were plotted for each of the inhibitors.

Determination of Proteolysis Inhibition in Live Cells Using Enzchek Substrate

A20 cells ($5 \times 10^6$/mL; 100 µL/well) were plated in a 96-well plate Inhibitors (28 µM in PBS+1% DMSO; 50 µL) were added to each wells and the cells were incubated at 37° C., 5% $CO_2$ for 30 minutes.

After this time Enzchek (Invitrogen, catalog number E6638, 20 μg/mL in DMEM+10% FCS) was added and the fluorescence emergence (excitation 485 nm; emission 530 nm) was measured every hour on a fluorescent plate reader at 37° C. Rates of fluorescence emergence were plotted for each of the inhibitors.

In Vitro Digest of Proteins with Purified Lysosomes

Lysosomes isolated from bone-marrow derived macrophages using a Percoll density-gradient fractionation (400 ng/μL, 3.6 μL) were resuspended in assay buffer (50 mM Citrate, pH 4.5, 0.5% Triton X-100; 59 μL) Inhibitor (70 μM; 12 μL in PBS+5% DMSO) was added and the mixture incubated for 15 minutes. Protein substrate (1 mg/mL in PBS, 9 μL) was added to the mixture and the reaction was incubated at 37° C. At the indicated timepoints 20 μL of the reaction mixture was removed and boiled with LDS-sample buffer and analysed by SDS-PAGE.

Determining the Effect of CPI on EGF-Signalling

COS7 cells growing in 12-well tissue culture plates were preincubated for 1 hour with or without cystatin C (0.35 mg/ml) or CPI (0.32 mg/ml) and then stimulated with 100 ng/ml EGF for the times shown. The cells were scraped from the well in 50 μl lysis buffer containing 50 mM Tris, 150 mM NaCl, 1 mM EGTA, 1 mM EDTA, 1% NP40 plus protease inhibitors (Roche, Miniprotease tablet). Aliquots were heated in SDS sample buffer and run on a 4×12% MOPS % gel (Invitrogen). After transfer to Hybond ECL membrane EGF receptor was revealed with a rabbit anti-EGF receptor antibody (Santa Cruz) followed by peroxidase conjugated donkey anti-rabbit (Jackson) and a standard ECL protocol (Millipore). The blot was then stripped and reprobed for phosphor-Erk (p42/44 MAP kinase; Cell signalling) and as as loading control, Rsk2 (Santa Cruz) with appropriate secondary antibodies. The signals were quantitated using ImageJ analysis software.

Immunofluorescence (IF) Microscopy

IF was performed according to standard protocols. For visualization of fluorescent substrate processing (Enzchek, vide infra), murine A20 B-cell blasts were grown on coverslips and incubated with enzchek (1 μg/mL final concentration) in presence or absence of protease inhibitors as indicated (20 μM) for 5 hours under standard growth conditions. Following treatment, cells were fixed with 3.7% paraformaldehyde in PBS, Triton X-100 permeabilized (0.1% in PBS), and immunostained against CD63, visualized using an anti-mouse secondary antibody-Alexa 647 conjugate on a Leica SP-2 confocal microscope using a 63× magnification objective.

Analysis of EGFR endocytosis and trafficking was performed as previously described with the following modifications. HeLa cells were grown on coverslips and serum starved in the absence or presence of CPI (20 μM; 0.1% FCS in DMEM-PBS 1:1) and stimulated with EGF (100 ng/mL final concentration) for 5 or 90 minutes. Samples were prepared as previously described. All images were collected using a Leica SP-2 confocal microscope equipped with a 63× magnification objective. Post-image processing and data analysis were performed using ImageJ. Image quantification was based on 25-50 cells per condition per experiment and significance was calculated using a standard Student's T-test.

Synthesis and Analysis of a Model Vaccine Consisting of Model Antigen and Protease Inhibitor A vaccine construct was synthesized by conjugating both the model antigen ovalbumin and an inhibitor of all three classes of protease to a solid phase adjuvant.

Conjugation of his-Tagged Proteins to Iron Oxide Nanoparticles

Talon-modified iron oxide beads were dissolved in 500 μL of 100 mM phosphate buffer, 600 mM NaCl; pH 8.0 with 0.02% Tween 20. Ovalbumin-6His was added (0.3 nmol; 20 μL of a 0.23 mg/mL solution, serially diluted 1:2) was added and the mixture was shaken (1000 rpm) at room temperature for 2 hours. The sample was then split into 2 equal portions. One portion was left shaking. To the other portion was added 0.3 nmol of Cystatin-Pepstatin-conjugate-6His. The solutions were then left shaking for a further 2 hours.

After this period the particles were collected in a Dynal-particle concentrator magnet (MPC-S) and resuspended in PBS (1.5 mL). The particles were reconcentrated and washed with a further 3 portions of PBS. The purified particles were resuspended in 50 μl of PBS.

Determining the Amount of Iron in the Vaccine Preparates

Iron content of modified particles was determined using a bathophenantroline assay, based on that reported by Perry et al.[31]

Determining Ovalbumin and Protease Inhibitor Loading

150 μg of particles (30 μL) were diluted with LDS-sample buffer (Invitrogen; NuPAGE) and analysed on a 12% NuPAGE SDS-gel (Invitrogen). The protein content was transferred to a nitrocellulose membrane by semi-dry transfer.

The membrane was blocked with 5% w/v skimmed milk powder in PBS with 0.1% Tween 20 for 1 hour at room temperature. After this time a solution of anti-Ovalbumin (Polysciences, 2344-5, 5 mg/mL, 1:5000 dilution) was added in 5% skimmed milk powder in PBS-Tween 20 and the membrane was gently shaken at 4° C. for 17 hours. After this period the gel was washed 3 times with PBS-Tween and incubated with secondary pig-anti-rabbit-horseradish peroxidase conjugate (1:3000 in 5% skimmed milk powder in PBS-Tween 20 at room temperature for 1 hour. The membrane was washed 4 times with PBS-Tween before visualising the presence of HRP with ECL Western Blotting Detection Reagent (GE Healthcare) and exposure to photographic film.

The density of the bands was normalised against a standard curve of ovalbumin of known concentrations using Totallab gel analysis software (Nonlinear Dynamics, Newcastle upon Tyne, UK) to approximate the loading of ovalbumin on the particles.

Cystatin-levels and cystatin-pepstatin levels were determined using the Mouse anti-Human Cystatin C antibody (mouse anti-human Cystatin C, MAB1196, R&D Systems, 1:3000 dilution) using the above Western blot protocol.

OT-1 and OT-II Activation Assay 10,000 mouse bone marrow-derived dendritic cells were incubated with 0.1 mg of the Ovalbumin/inhibitor modified particles for 2 hours in a 96-well round-bottom plate. The cells were washed prior to the addition of 100,000 OT-I or OT-II T-cells (purified by negative selection) to each of the wells. After 3 days $^3$H-labeled thymidine was added and incorporation thereof measured.

CPI Enhancement of PLGA Encapsulated Ovalbumin

In vitro studies: Dendritic cells are incubated for 48-72 hours with the 3 varieties of PLGA microspheres (CPI only, Ovalbumin only and CPI/ovalbumin) in the presence of T cells able to detect the presentation of peptides derived from processed and presented antigen (OT1 and OTII). T cell activation is then measured by incorporation of 3H-thymidine during a 12-16 hour period.

In vivo studies: C57BL/6 mice were injected sub-cutaneously with the same PLGA microspheres (1.75 mg PLGA containing approx. 5% w/w ovalbumin) The injected volumes additionally contained 1 μg/ml LPS to activate antigen presenting cells at the site of injection. All mice previously (30-60 mins earlier) received $10^6$ CFSE labeled OT1 and OTII T cells. After 24-48 hours T cell proliferation in draining lymph nodes was measured by CFSE dilution.

DETAILED DESCRIPTION

Figure 2:
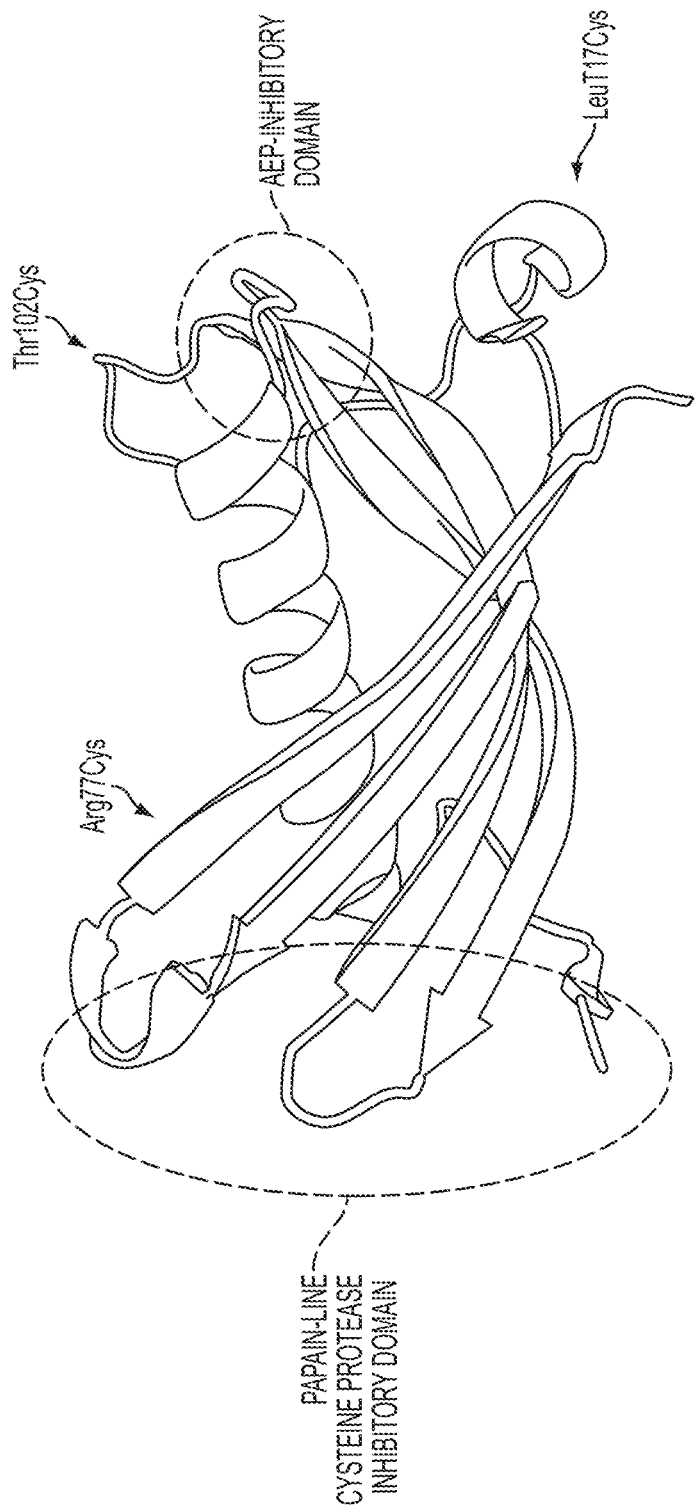
FIG. 2 is a representation that illustrates three different cystatin mutants which were tested. Mutation sites were picked for solvent accessibility, as well as for their location, with residues which are part of the inhibitory motifs (as highlighted by the dashed circles), excluded. Three mutations where chosen, one on a b-sheet (R77C), one on an a-helix (L117C) and on a non-structured loop region of the protein (T102C).
Figure 3:
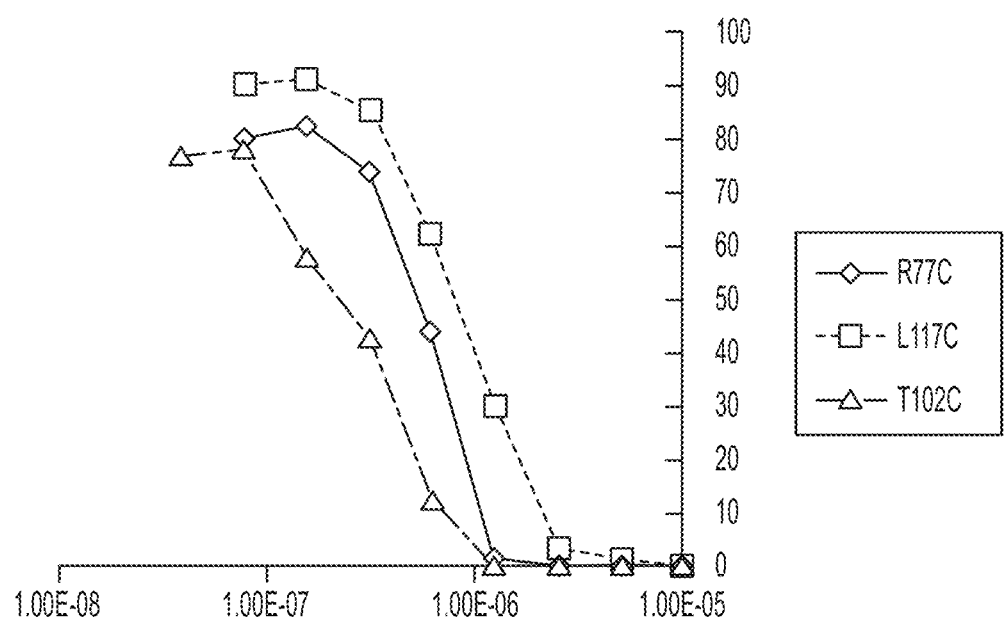
FIG. 3 is a graph that illustrates relative inhibitory rates of the three mutants as determined by serial dilution of the various cystatin C mutants (concentration in mM) in presence of 5 ng of Cathepsin L/well.
Figure 4A:
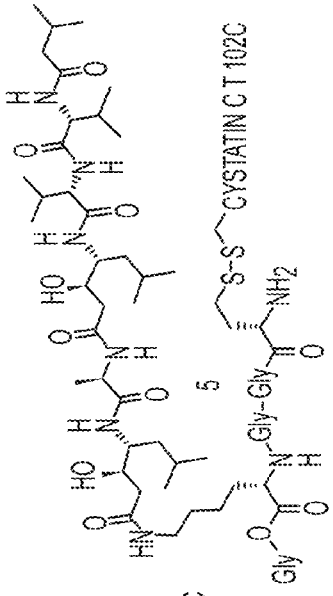
FIG. 4A-4D (SEQ. ID. NOS: 5 and 6) is a representation that illustrates 4 preferred oxide adjuvant. Equal amounts of modified iron oxide were analysed by Western blot against cystatin C and Ovalbumin Three different concentrations of Ovalbumin were loaded together with a fixed amount of cystatin c, pepstatin A or a cystatin-peptstatin inhibitor.
Figure 4B:
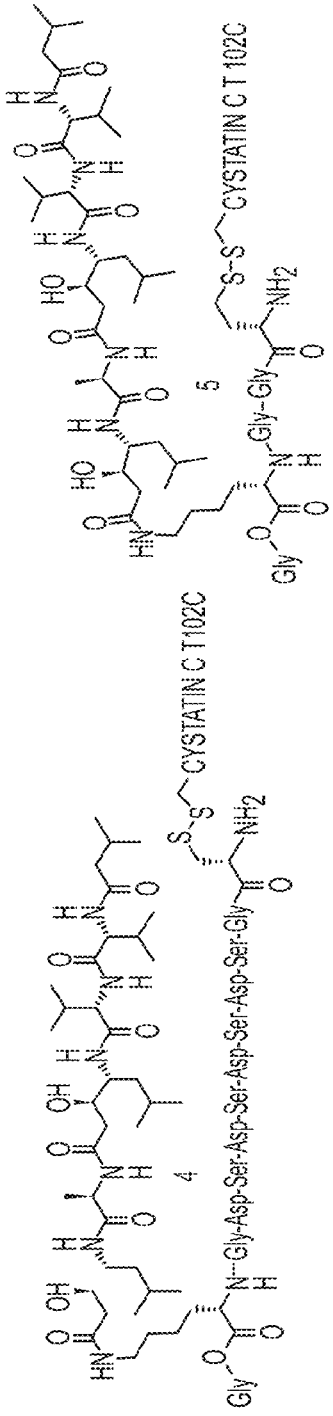
Figure 4C:
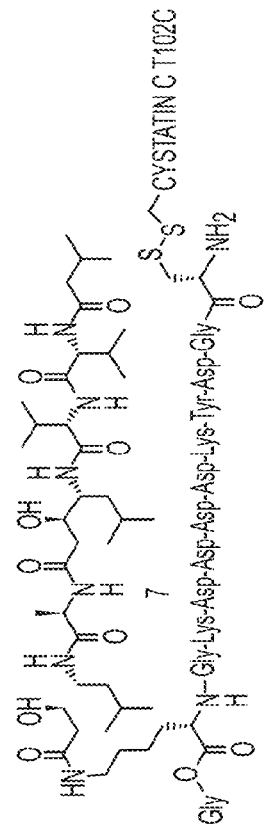
Figure 4D:
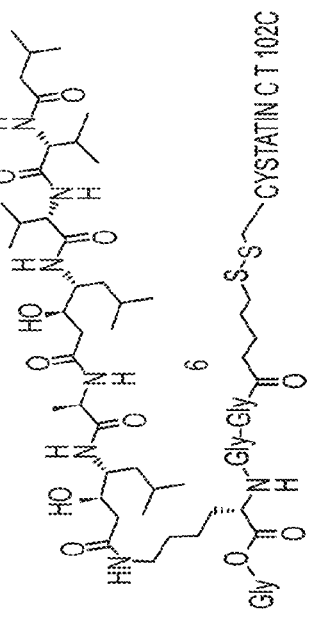
Figure 5:
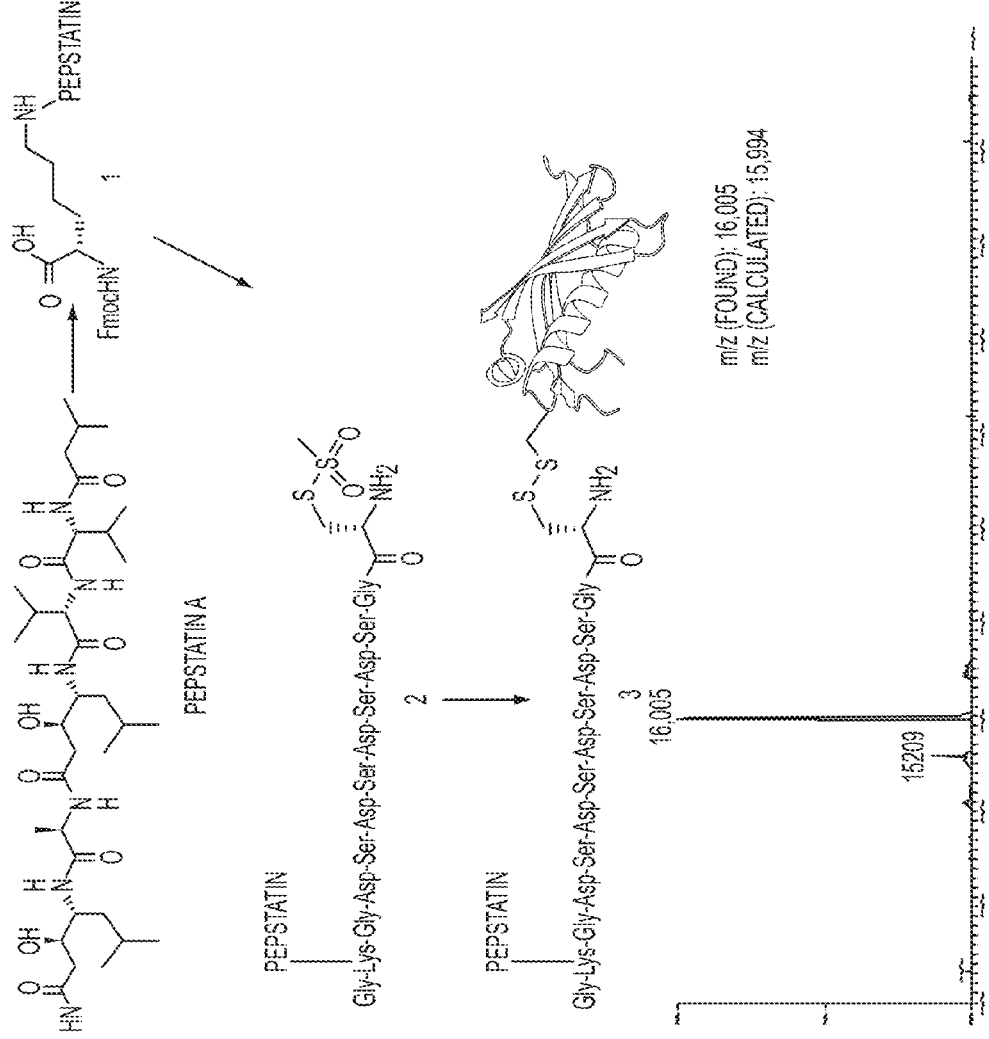

In one embodiment, the present invention provides a molecule which displays tight control over the stoichiometry and localization of the introduced pepstatin; with no more than one pepstatin molecule per cystatin at a site away from the inhibitory domains of cystatin c (see for example FIG. 2) this has been achieved through introduction of a free cysteine into the protein backbone of cystatin C by site-directed mutagenesis[25], as it can be selectively modified in presence of other nucleophilic residues. Issues associated with disulfide scrambling with the two exisiting disulfide bridges in cystatin C were avoided by using a mammalian expression system. Various mutants were tested (see Table 1 and FIG. 2), and T102C was found to have the most favourable inhibitory properties. A C-terminal 6His-tag was also introduced, for facilitating purification and possible conjugation of the inhibitor to a solid phase carrier.

In accordance with a preferred embodiment methanethiosulfonate chemistry was used to introduce the pepstatin onto the free cysteine of cystatin $C^{25b, 26}$, due to its high selectivity for sulfhydryls and its facile introduction into the peptide backbone through a MTS-Boc-Cysteine building block. Furthermore there is the potential for endosomal release of the pepstatin by reduction of disulfides by the lysosomal thiol reductase GILT[27].

As it has been reported that conjugation of the C-terminal end of pepstatin to lysine residues did not reduce its inhibitory potential significantly[23], the inventors decided to introduce a charged peptide between the pepstatin and the MTS group (FIGS. 4A-4D-7(A)-7(C)) to increase solubility of the conjugate. After mild reduction with, for example, 5 mM DTT (conditions to which the disulfide-bridges of cystatin C have been shown to be stable) of the free cysteine residue prior to coupling, the inventors obtained >95% protein recovery levels and >80% modification as determined by mass spectrometry (FIGS. 4A-4D-7(A)-7(C)). Any unreacted cystatin C could be readily separated from the CPI using HPLC purification.

Figure 8G:
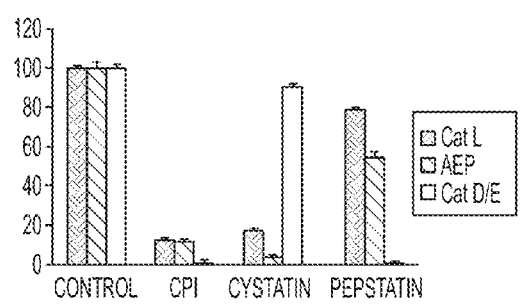
Figure 8H:
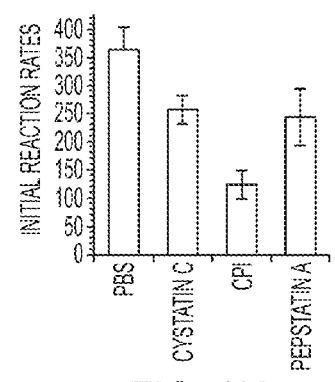

Next, the inhibitory capacity was analyzed against recombinant members of each of the three target protease families The CPI showed similar IC50 values against representative members of the three classes of endosomal protease even without reduction of the disulfide bond between cystatin C and pepstatin A (FIG. 8, panel (A)-(C)). Moreover, the CPI was able to inhibit the same 3 classes of protease activity present in dendritic cell lysates (FIG. 8, panel (D)-(F)). Most importantly, when the CPI conjugate was incubated with A20 cells and their protease activity determined using the Enzcheck substrate, the inventors found that the probe could simultaneously abolish cathepsin D/E activity as well as reduce PLCP and AEP activity by (FIG. 8, panel G) with no cell death occurring (as determined by trypan blue assay).

One of the potential therapeutic applications of the CPI is as a modulator of antigen processing. It has been reported that unstable antigens can be over-processed in the endo-lysosomal pathway leading to a reduction in antigen presentation[28] and that protease resistant antigens frequently make for better immunogens. The inventors tested whether these unstable antigens could be 'protected' from lysosomal over-degradation by the CPI with the eventual aim of improving antigen presentation of such unstable antigens in vaccine preparations.

In recent studies by Delamarre et al it was demonstrated that a destabilized variant of horseradish peroxidase (apo-HRP) from which the heme-group had been removed was more sensitive than heme containing HRP to proteolysis in vitro and gave a much weaker immune response in vivo. The authors suggested that heme-free HRP was too rapidly degraded by the antigen processing machinery, preventing efficient loading of MHC-complexes.

Figure 9:
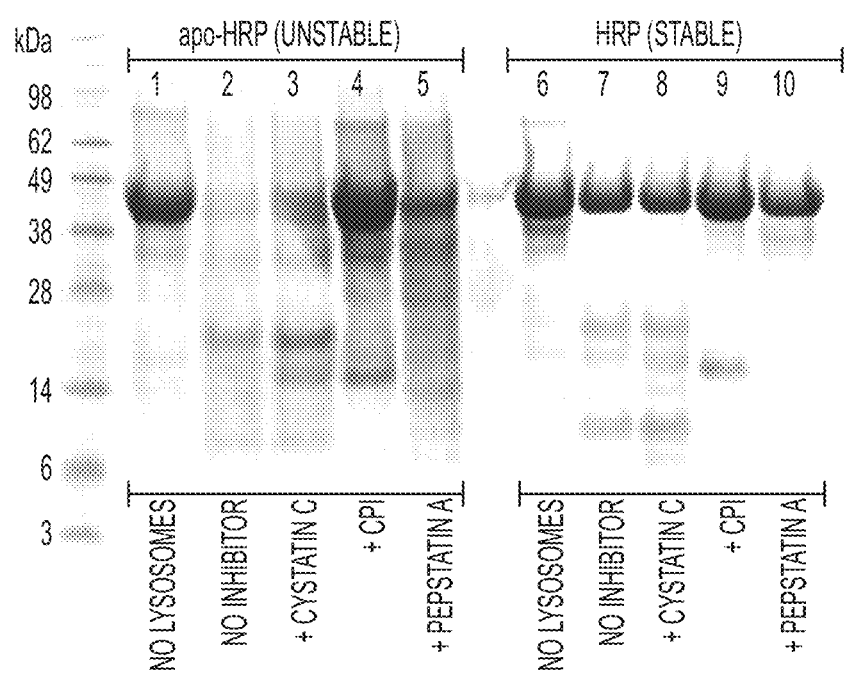

The inventors tested whether it was possible to protect unstable apo-HRP from lysosomal degradation in vitro by adding a CPI to the invention. As a source of endo-lysosomal proteases the inventors used purified lysosomes from mouse macrophages as they express high levels of all these enzymes. Indeed, even before the first measurement apo-HRP was fully degraded by macrophage endo/lysosomes (FIG. 9). Addition of cystatin alone or pepstatin alone caused little or no stabilization of apo-HRP, indicating a functional redundancy between the lysosomal enzymes in these macrophages. When a CPI was added, however, apo-HRP was as stable to lysosomal digestion as wt-HRP (FIG. 9). These results suggest that incorporation of a CPI into immunological adjuvants for unstable antigens may be worthwhile and is currently under investigation.

The inventors next assessed the capacity of CPI to inhibit endo/lysosomal proteases in live cells and whether a CPI could successfully modulate the biological functions of this compartmental system. One important role of the endocytic pathway is to degrade activated growth factor receptors following their ligand-stimulated endocytosis. For example, following the EGF receptor (EGFr) being ubiquitinated, it is clustered in clathrin coated pits and delivered to the endosome system where it becomes sequestered on the internal vesicles of multivesicular bodies (MVBs) preventing recycling and shutting down its capacity to signal[29]. MVBs then fuse with lysososomes and the EGF receptor is degraded; The specific lysosomal proteases remain to be fully defined.[11,35].

Figure 10A:
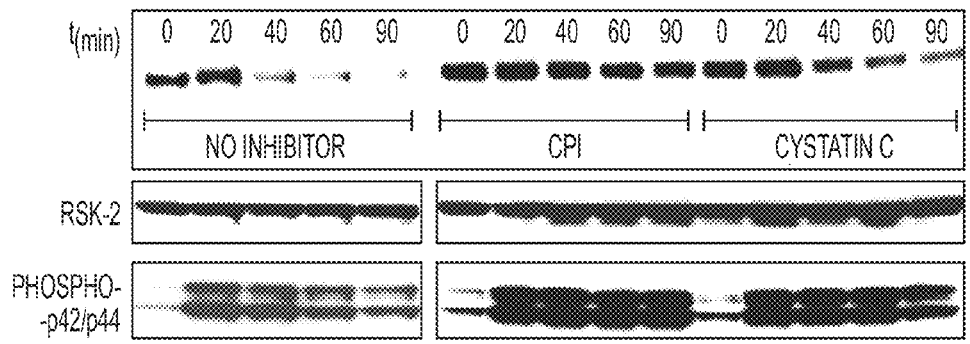
Figure 10B:
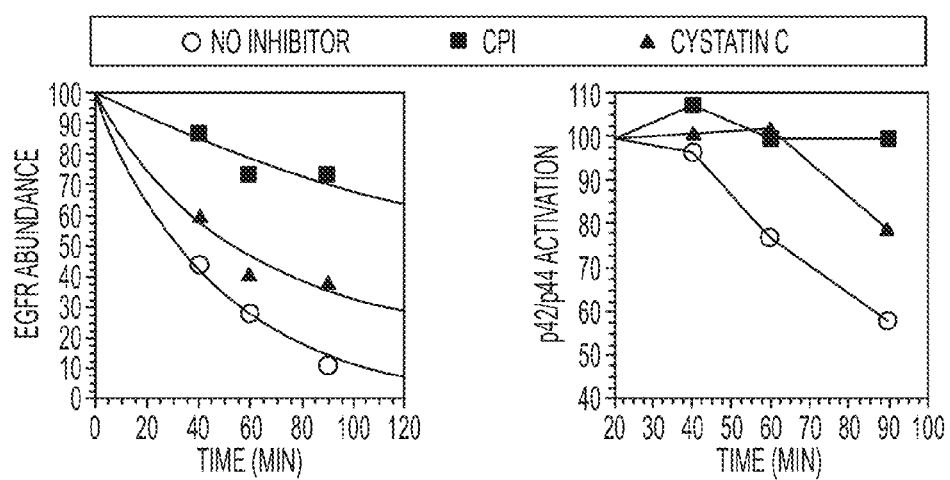
Figure 11A:
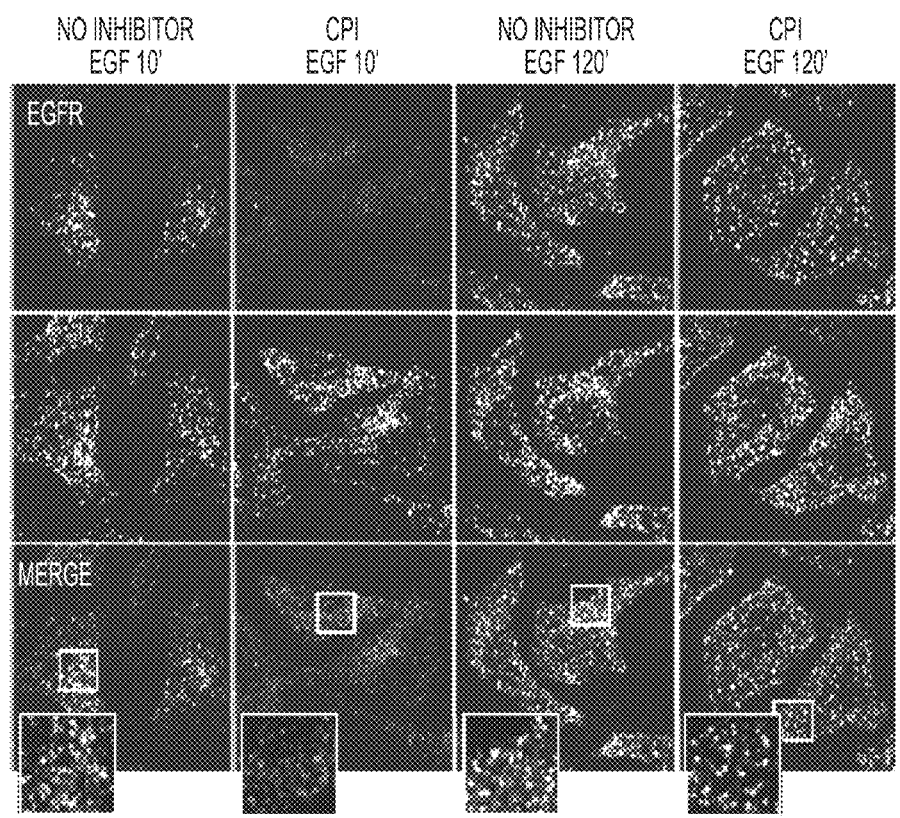
Figure 11B:
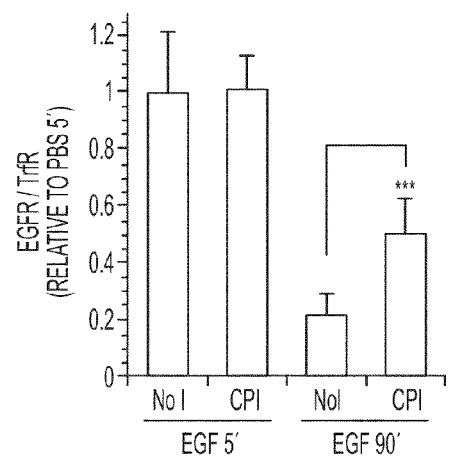
Figure 11C:
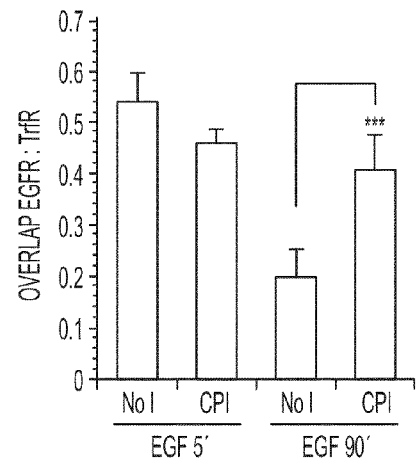

The inventors precincubated the EGFr positive kidney cell line COS-7 in the presence or absence of a CPI or cystatin C (the insolubility of pepstatin A prevented this compound from giving meaningful data in this experiment) and then challenged with EGF. At different times the level of EGFr remaining was monitored by western blotting (FIG. 10). In control cells downregulation of EGFr was evident after 40 minutes and virtually complete after 90 minutes (FIG. 10A-10B). In contrast levels of EGFr were much more persistent in Cos7 cells preincubated with CPI demonstrating a block in receptor degradation as quantified in FIG. 11A-11C.

Preincubation with cystatin also suppressed EGFr downregulation but not to the same extent as CPI indicating that both cysteine and aspartyl proteases are involved in EGFr processing. The arrest in receptor processing was not due to inhibitor toxicity since the MAP kinases Erk1/2 were activated 5 normally in CPI and cystatin treated cells. In fact, there was more sustained Erk activation in CPI treated cells consistent with the persistence of EGFr (FIG. 10A-10B, 2nd panel). Thus, CPI is taken up by cells and can suppress key proteolytic events within the endo/lysosomal system.

Figure 6:
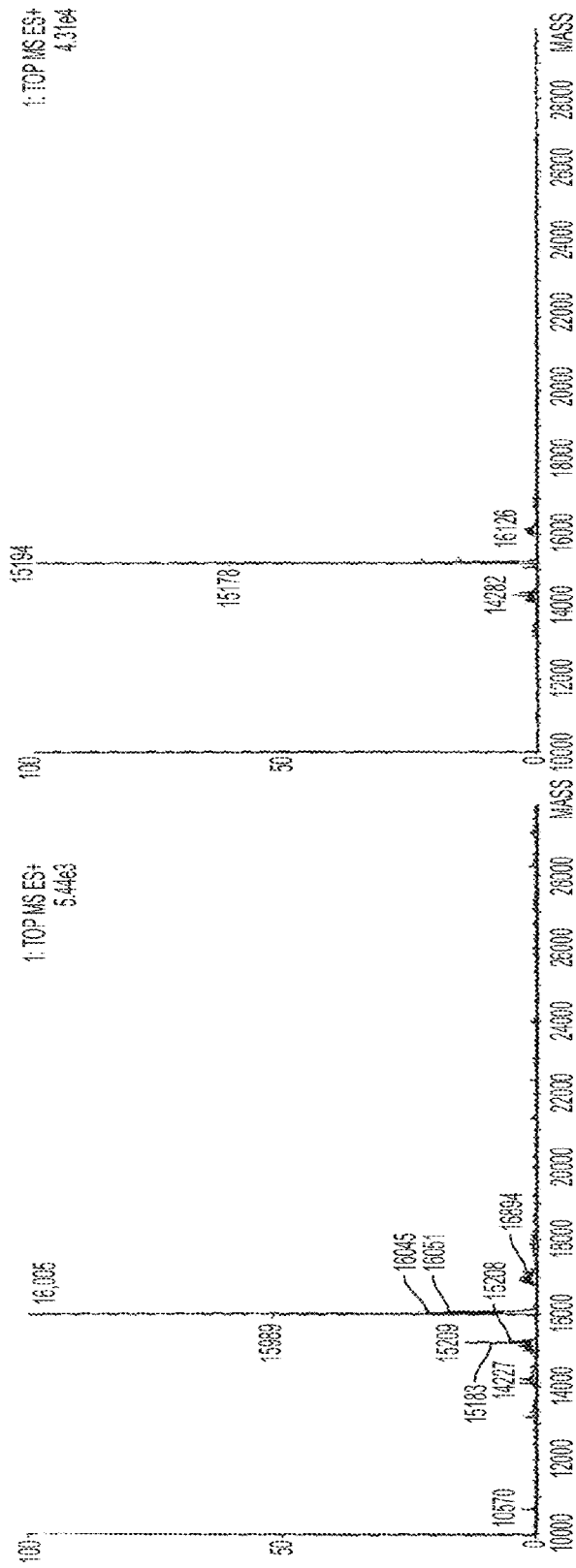
Figure 7A:
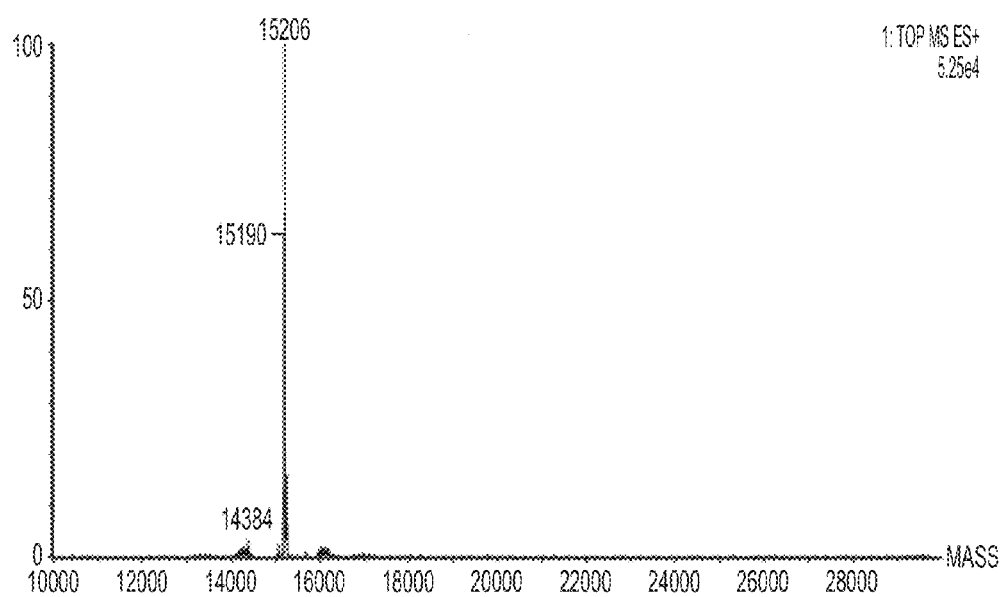
Figures 7B, 7C:
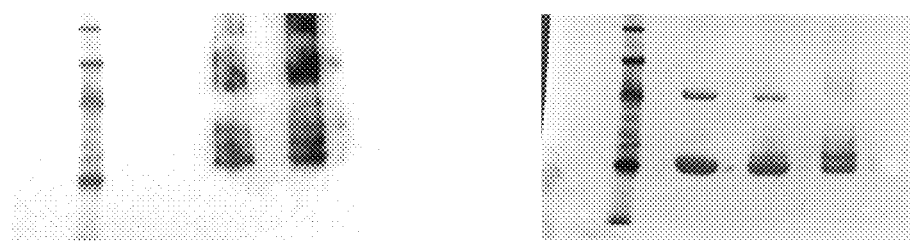
Figure 12:
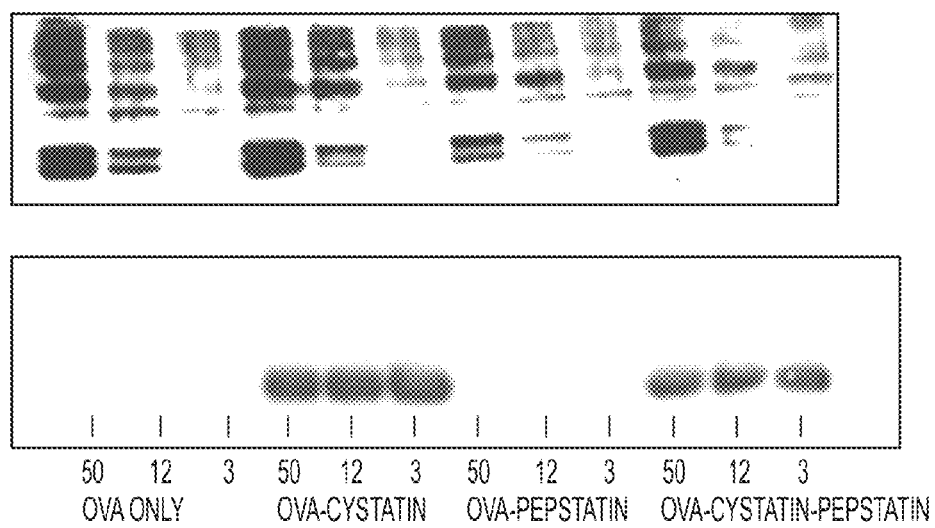
Figure 13A:
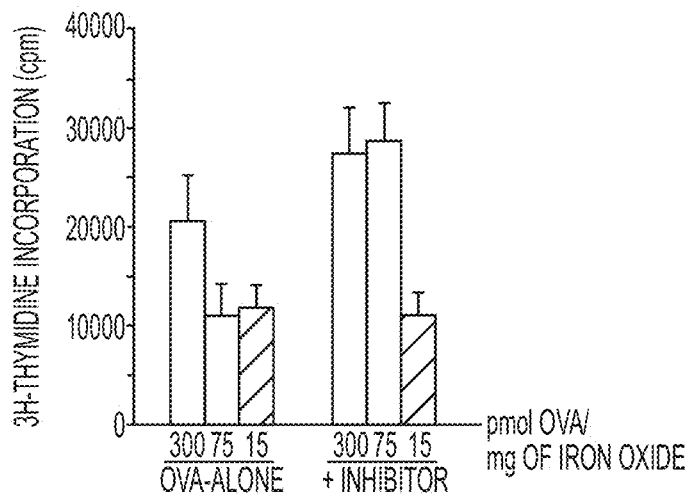
FIG. 13A-13B is are graphs that illustrate the responses of (A) OT-I (top) and (B) OT-II (bottom) T-cells to dendritic cells incubated with constructs carrying three different amounts of Ovalbumin, as determined in FIG. 12 a with or without protease inhibitor.
Figure 13B:
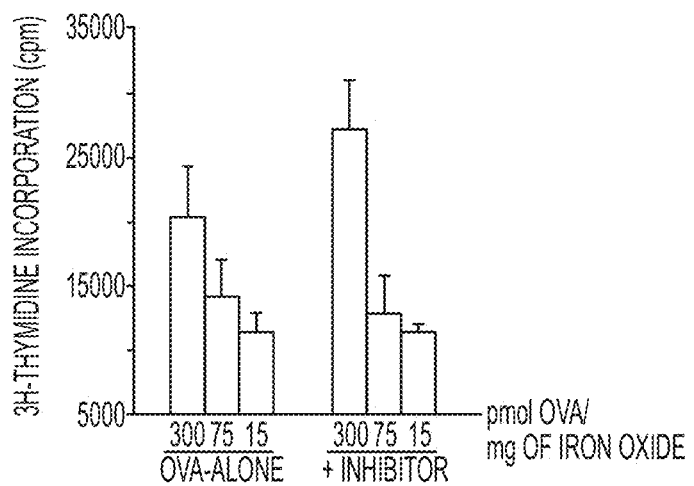
Figure 14A:
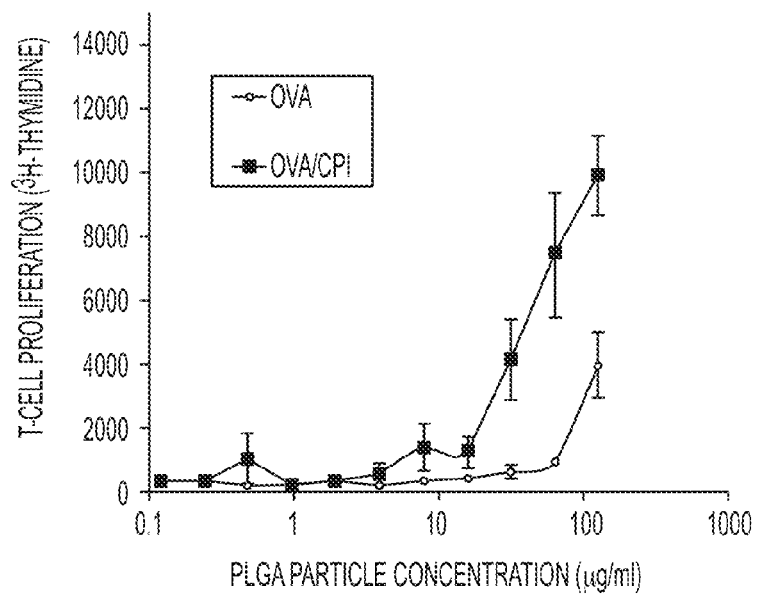
FIG. 14A-14B are graphs that illustrate the improved antigen presentation on class I MHC (cross-presentation) by co-encapsulation of antigen with CPI. PLGA microspheres were titrated in 96-well plates and ovalbumin presentation measured by the addition of murine bone marrow derived dendritic cells (~5×10$^4$/well) and OTI T cells (~5×10$^2$/well). (A) After ~72 hours T cell proliferation was measured by addition of 1 µCi 3H-thymidine. Cells were harvested 16 hours later and $^3$H incorporation measured by scintillation counting. Alternatively (B) an aliquot of the supernatant was removed after 72 hours and IL-2 production measured by standard ELISA assay.
Figure 14B:
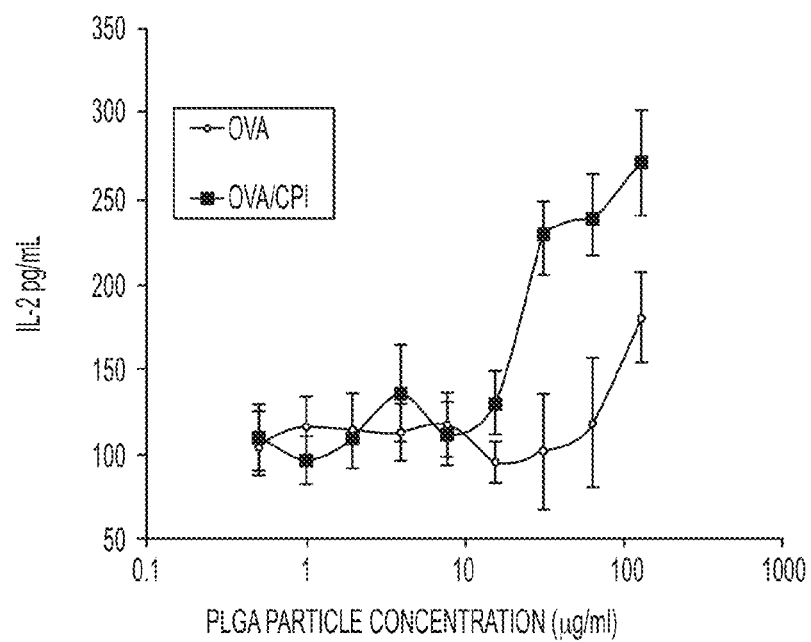
Figure 15:
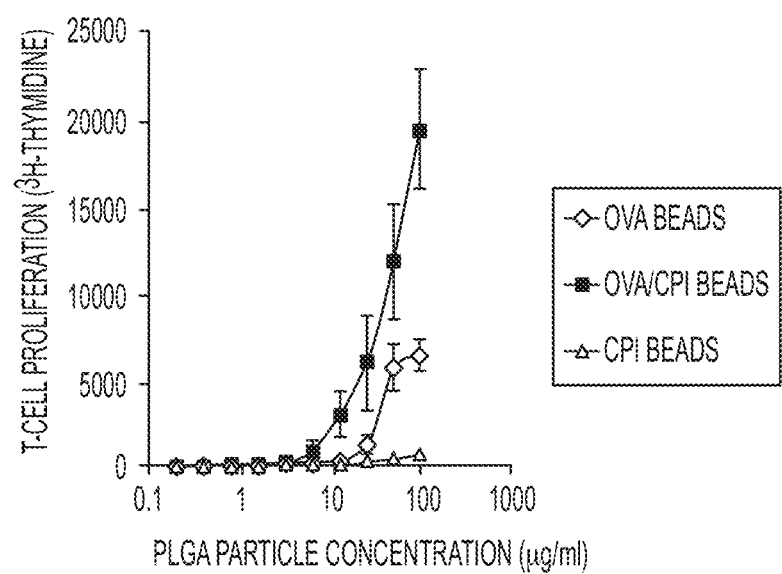
FIG. 15 is a graph that illustrates the Improved antigen presentation on class II MHC by co-capsulation of antigen with CPI. Conditions similar to those in FIG. 14A-14B except that OTII (class II MHC restricted) T cells were used instead of OTI.
Figure 16A:
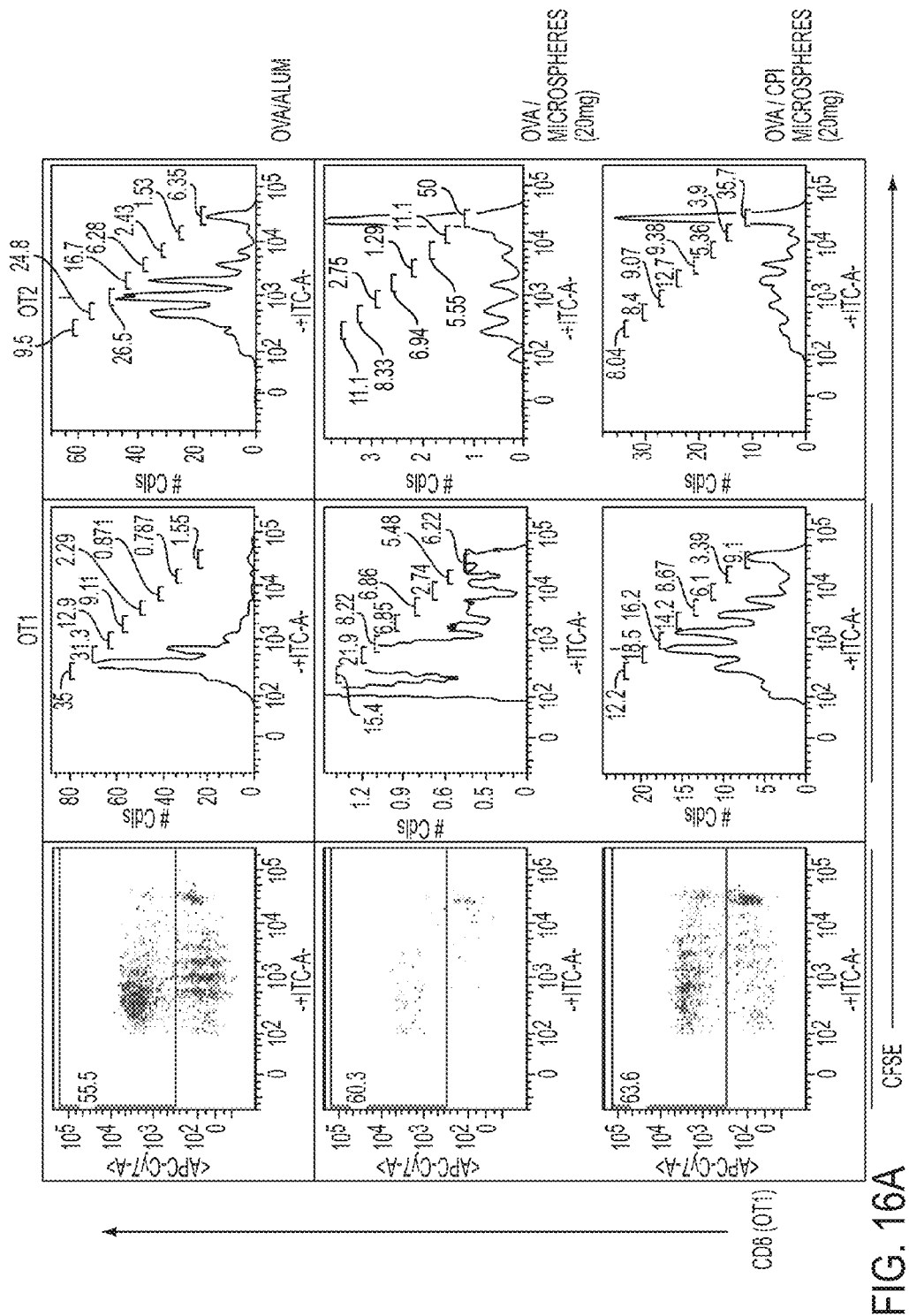
FIG. 16A-16B are graphs that illustrate the improved presentation of the ovalbumin antigen in vivo by co-encapsulation with CPI. C57BL/6 mice were immunised with different varieties of ovalbumin-containing PLGA microspheres and were additionally loaded with CFSE labelled T cells (see Methods outline). As a positive control ovalbumin was admixed with the strong adjuvant alum. T cell proliferation was subsequently measured by CFSE dilution in the lymph nodes draining the site of injection (sub-cut. base of tail). (A) T cells were also stained with anti-CD8 antibodies to distinguish OT1 from OTII cells. Leftmost panels show raw FACS data while centre and right panels show histograms of T cell numbers at different cell doublings for OTI (centre) and OTII (right). (B) total accumulated T cells by integration of cell doubling data. The data reveal a hierarchy of expansion for both OT1 and OTII. As expected Ova/Alum promoted the strongest expansion while Ova/CPI PLGA promoted stronger expansion than Ova PLG.
Figure 16B:
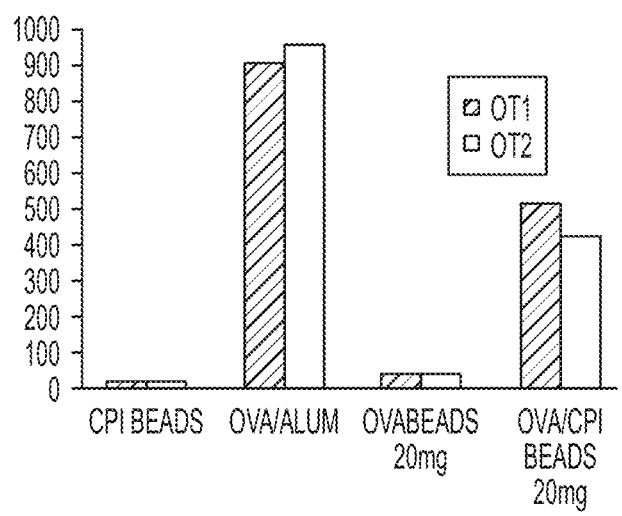

The inventors also tested the protease inhibitor in a model vaccine. First, defined amounts of antigen (Ovalbumin) and inhibitor (FIG. 12) were loaded onto a solid-phase carrier not unlike those used in commercial vaccine preparations. Next these vaccine preparates were fed to mouse dendritic cells for 2 hours. After washing, purified OT-I and OT-II T-cells specific for epitopes on Ovalbumin were added and an improved response of the OT-I and OT-II T-cells could be observed (FIG. 13(A-)13(B)). FIGS. 6c and d show that the inclusion of CPI substantially improves presentation of the ovalbumin antigen. Beads containing CPI alone produced no T cell proliferation (not shown. Moreover, a Ova/CPI PLGA (+LPS) formulation produces more potent antigen presentation than the Ova PLGA (+LPS) formulation in vivo (see FIG. 16(A)-16(B)). This shows that, in principle, the pan-endosomal protease inhibitor can improve antigen presentation in relevant immune cells.

Figure 17:
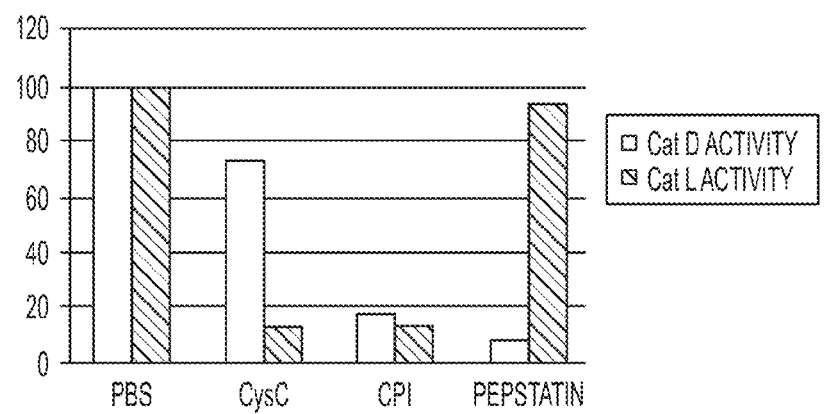
FIG. 17 is a graph that illustrates inhibition of cysteine protease activity and aspartyl protease activity in *T. brucei* cell lysates as determined using substrates specific for either cathepsin B/L/S like activity or cathepsin D/E like activity.
Figure 18:
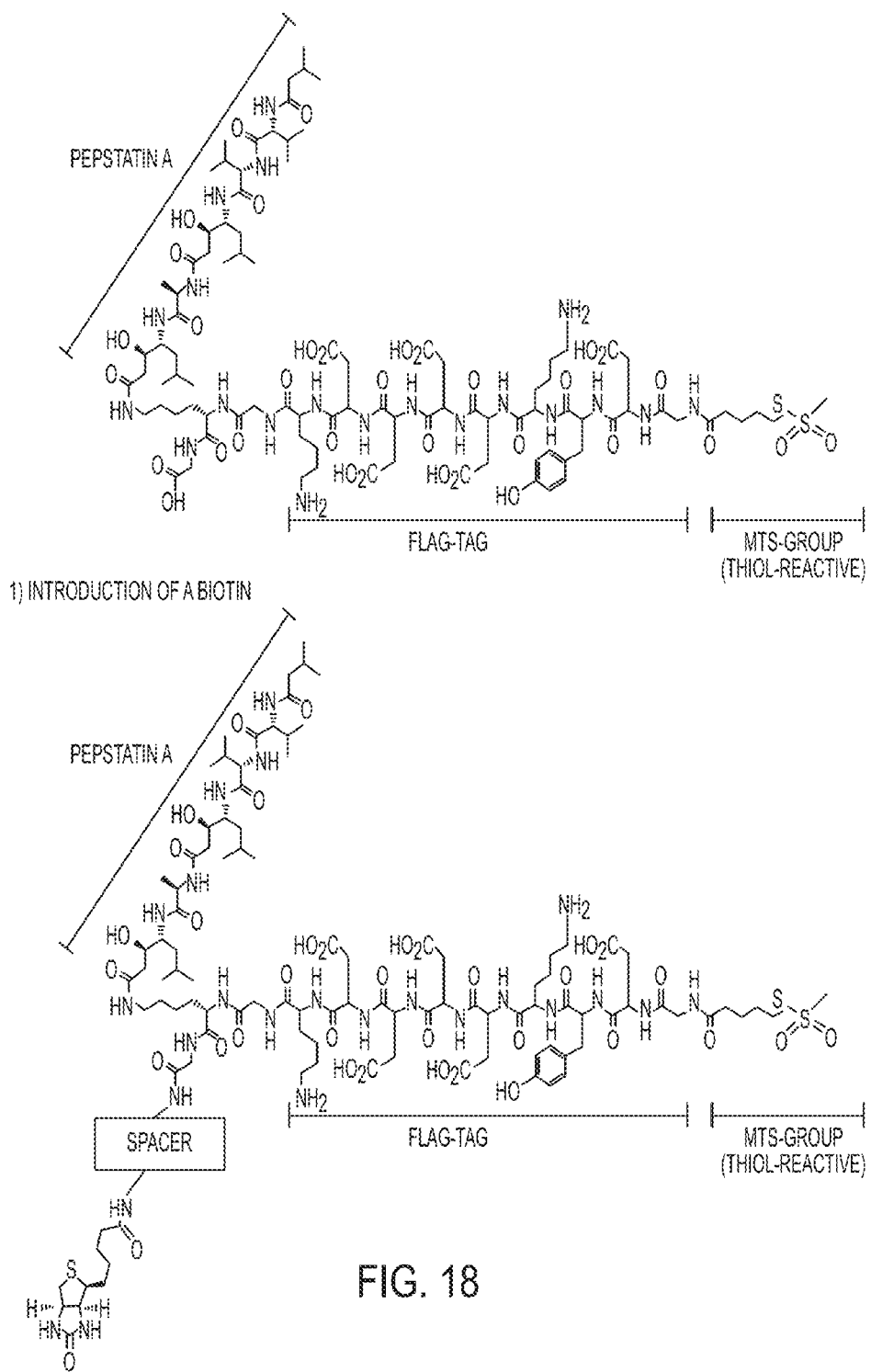
FIG. 18 is an illustration that represents some constructs that can be used for linking the protease inhibitor to another moiety, for example a targeting group, or a complex with a targeting group.
Figure 18:
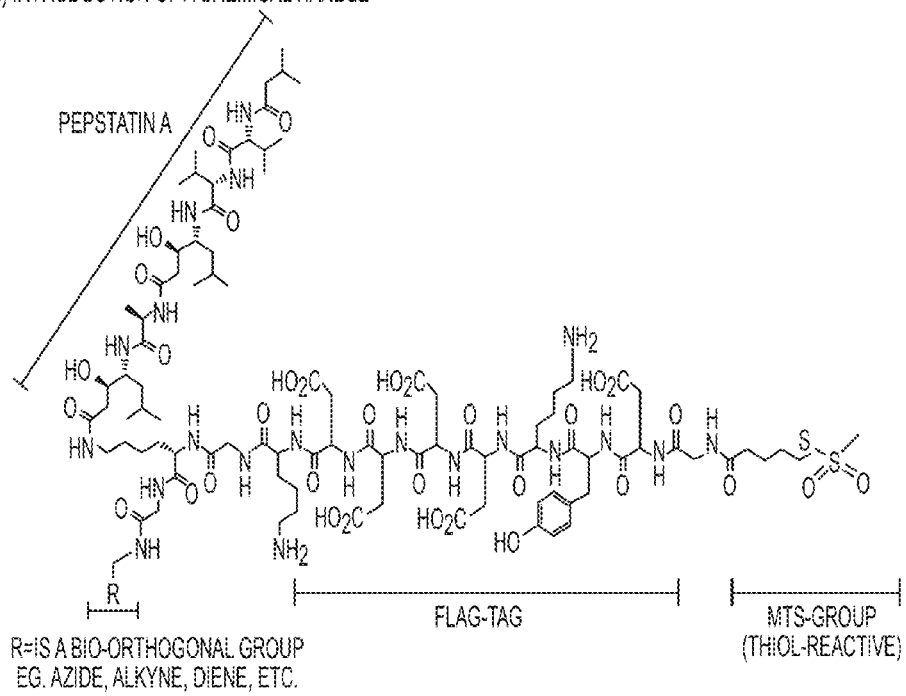
Figure 18:
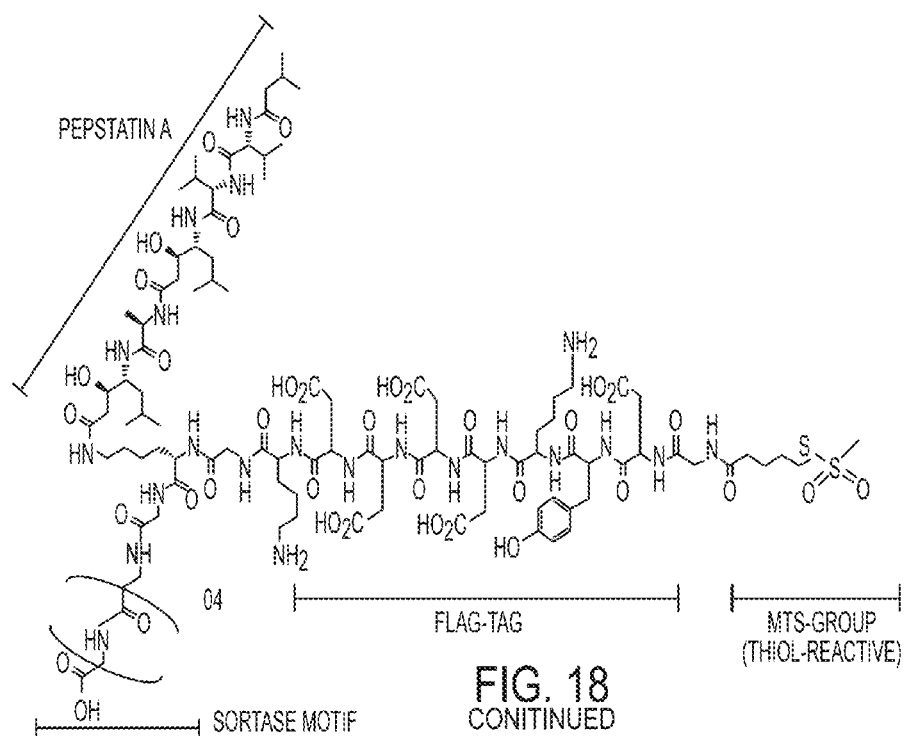

It was also tested whether the pan protease inhibitor could inhibit the proteolytic activity of pathogenic species, more specifically that of the trypanosomes. It was indeed observed that all three families of protease activities from *T. brucei* could be powerfully inhibited (FIG. 17).

In summary, the inventors have presented the construction of a single molecular entity that inhibits all three major families of endo/lysosomal proteases. This broad inhibition has been shown to attenuate destructive processing of labile proteins in vitro and to attenuate proteolytic events within the endo/lysosomal pathway in vivo.

REFERENCES

1. Leung, D.; Abbenante, G.; Fairlie, D. P., Protease inhibitors: Current status and future prospects. *J. Med. Chem.* 2000, 43 (3), 305-341.
2. Richardson, P. G.; Sonneveld, P.; Schuster, M. W.; Irwin, D.; Stadtmauer, E. A.; Facon, T.; Harousseau, J. L.; Ben-Yehuda, D.; Lonial, S.; Goldschmidt, H.; Reece, D.; San-Miguel, J. F.; Blade, J.; Boccadoro, M.; Cavenagh, J.; Dalton, W. S.; Boral, A. L.; Esseltine, D. L.; Porter, J. B.; Schenkein, D.; Anderson, K. C., Bortezomib or high-dose dexamethasone for relapsed multiple myeloma. *New Engl. J. Med.* 2005, 352 (24), 2487-2498.
3. Reiser, J.; Adair, B.; Reinheckel, T., Specialized roles for cysteine cathepsins in health and disease. *J. Clin. Invest.* 2010, 120 (10), 3421-3431.
4. Doyle, P. S.; Sajid, M.; O'Brien, T.; DuBois, K.; Engel, J. C.; Mackey, Z. B.; Reed, S., Drugs targeting parasite lysosomes. *Curr. Pharm. Design* 2008, 14 (9), 889-900.
5. Palermo, C.; Joyce, J. A., Cysteine cathepsin proteases as pharmacological targets in cancer. *Trends Pharm. Sci.* 2008, 29 (1), 22-28.
6. Briggs, J. J.; Haugen, M. H.; Johansen, H. T.; Riker, A. I.; Abrahamson, M.; Fodstad, O.; Maelandsmo, G. M.; Solberg, R., Cystatin E/M suppresses legumain activity and invasion of human melanoma. *BMC Cancer* 2010, 10.
7. Colbert, J. D.; Matthews, S. P.; Miller, G.; Watts, C., Diverse regulatory roles for lysosomal proteases in the immune response. *Eur. J. Immunol.* 2009, 39 (11), 2955-2965.
8. Keppler, D., Towards novel anti-cancer strategies based on cystatin function. *Cancer Letters* 2006, 235 (2), 159-176.
9. Henskens, Y. M.; Veerman, E. C.; Nieuw Amerongen, A. V., Cystatins in health and disease. *Biol. Chem.* 1996, 377 (2), 71-86.
10. Nicotra, G.; Manfroi, F.; Follo, C.; Castino, R.; Fusco, N.; Peracchio, C.; Kerim, S.; Valente, G.; Isidoro, C., High expression of cathepsin D in non-Hodgkin's lymphomas negatively impacts on clinical outcome. *Dis. Markers* 2010, 28 (3), 167-83.
11. Liaudet-Coopman, E.; Beaujouin, M.; Derocq, D.; Garcia, M.; Glondu-Lassis, M.; Laurent-Matha, V.; Prebois, C.; Rochefort, H.; Vignon, F., Cathepsin D: newly discovered functions of a long-standing aspartic protease in cancer and apoptosis. *Cancer Lett.* 2006, 237 (2), 167-79.
12. Delamarre, L.; Couture, R.; Mellman, I.; Trombetta, E. S., Enhancing immunogenicity by limiting susceptibility to lysosomal proteolysis. *J. Exp. Med.* 2006, 203 (9), 2049-2055.
13. Moss, C. X.; Villadangos, J. A.; Watts, C., Destructive potential of the aspartyl protease cathepsin D in MHC class II-restricted antigen processing. *Eur. J. Immunol.* 2005, 35 (12), 3442-3451.
14. Matthews, S. P.; Werber, I.; Deussing, J.; Peters, C.; Reinheckel, T.; Watts, C., Distinct Protease Requirements for Antigen Presentation In Vitro and In Vivo. *J. Immunol.* 2010, 184 (5), 2423-2431.
15. (a) Dennemarker, J.; Lohmüller, T.; Midler, S.; Aguilar, S. V.; Tobin, D. J.; Peters, C.; Reinheckel, T., Impaired turnover of autophagolysosomes in cathepsin L deficiency. *Biol. Chem.* 2010, 391 (8), 913-922; (b) Bednarski, E.; Ribak, C. E.; Lynch, G., Suppression of cathepsins B and L causes a proliferation of lysosomes and the formation of meganeurites in hippocampus. *J. Neurosci.* 1997, 17 (11), 4006-4021.
16. Turk, B.; Turk, D.; Turk, V., Lysosomal cysteine proteases: More than scavengers. *Biochim. Biophys. Act.* 2000, 1477 (1-2), 98-111.
17. Manoury, B.; Hewitt, E. W.; Morrice, N.; Dando, P. M.; Barrett, A. J.; Watts, C. An asparaginyl endopeptidase processes a microbial antigen for class II MHC presentation. *Nature* 1998, 396 (6712), 695-699.
18. (a) Otto, H.-H.; Schirmeister, T., Cysteine Proteases and Their Inhibitors. *Chem. Rev.* 1997, 97 (1), 133-172; (b) Rozman-Pungercar, J.; Kopitar-Jerala, N.; Bogyo, M.; Turk, D.; Vasiljeva, O.; Stefe, I.; Vandenabeele, P.; Bromme, D.; Puizdar, V.; Fonovi, M.; Trstenjak-Prebanda, M.; Dolenc, I.; Turk, V.; Turk, B., Inhibition of papain-like cysteine proteases and legumain by caspase-specific inhibitors: when reaction mechanism is more important than specificity. *Cell Death Differ* 0000, 10 (8), 881-888.
19. Abrahamson, M.; Alvarez-Fernandez, M.; Nathanson, C. M., Cystatins. *Biochem Soc Symp* 2003, (70), 179-99.
20. Alvarez-Fernandez, M.; Barrett, A. J.; Gerhartz, B.; Dando, P. M.; Ni, J.; Abrahamson, M., Inhibition of mammalian legumain by some cystatins is due to a novel second reactive site. *J. Biol. Chem.* 1999, 274 (27), 19195-19203.
21. Umezawa, H.; Aoyagi, T.; Morishima, H.; Matsuzaki, M.; Hamada, M., Pepstatin, a new pepsin inhibitor produced by Actinomycetes. *J. Antibiot.* 1970, 23 (5), 259-262.
22. Furuno, K.; Miwa, N.; Kato, K., Receptor-mediated introduction of pepstatin-asialofetuin conjugate into lysosomes of rat hepatocytes. *J. Biochem* 1983, 93 (1), 249-256.
23. Brygier, J.; Vlncentelli, J.; Nljs, M.; Guermant, C.; Paul, C.; Baeyens-Volant, D.; Looze, Y., Preparation and preliminary characterization of poly(ethylene glycol)-pepstatin conjugate. *App. Biochem. Biotech.* 1994, 47 (1), 1-10.
24. (a) Free, P.; Hurley, C. A.; Kageyama, T.; Chain, B. M.; Tabor, A. B., Mannose-pepstatin conjugates as targeted inhibitors of antigen processing. *Org. Biomol. Chem.* 2006, 4 (9), 1817-1830; (b) Raiber, E. A.; Tulone, C.; Zhang, Y.; Martinez-Pomares, L.; Steed, E.; Sponaas, A. M.; Langhorne, J.; Noursadeghi, M.; Chain, B. M.; Tabor, A. B., Targeted delivery of antigen processing inhibitors to antigen presenting cells via mannose receptors. *ACS Chem. Biol.* 2010, 5 (5), 461-476.
25. (a) Chen, C. S.; Chen, W. N. U.; Zhou, M.; Arttamangkul, S.; Haugland, R. P., Probing the cathepsin D using a BODIPY FL-pepstatin A: Applications in fluorescence polarization and microscopy. *J. Biochem. Biophys. Met.* 2000, 42 (3), 137-151; (b) Zaidi, N.; Burster, T.; Sommandas, V.; Herrmann, T.; Boehm, B. O.; Driessen, C.; Voelter, W.; Kalbacher, H., A novel cell penetrating aspartic protease inhibitor blocks processing and presentation of tetanus toxoid more efficiently than pepstatin A. *Biochem. Biophys. Res. Comm.* 2007, 364 (2), 243-249.
26. Popp, M. W.; Ploegh, H. L., Making and breaking peptide bonds: protein engineering using sortase. *Angew Chem Int Ed Engl* 2011, 50 (22), 5024-32.
27. Hopp, T. P.; Prickett, K. S.; Price, V. L.; Libby, R. T.; March, C. J.; Pat Cerretti, D.; Urdal, D. L.; Conlon, P. J., A Short Polypeptide Marker Sequence Useful for Recombinant Protein Identification and Purification. *Nat Biotech* 1988, 6 (10), 1204-1210.
28. van Kasteren, S. I.; Kramer, H. B.; Gamblin, D. P.; Davis, B. G., Site-selective glycosylation of proteins: creating synthetic glycoproteins. *Nature protocols* 2007, 2 (12), 3185-3194.
29. (a) Auerswald, E. A.; Nagler, D. K.; Assfalgmachleidt, I.; Stubbs, M. T.; Machleidt, W.; Fritz, H., Hairpin loop mutations of chicken cystatin have different effects on the inhibition of Cathepsin B, Cathepsin L and Papain. *FEBS Lett.* 1995, 361 (2-3), 179-184; (b) Bjork, I.; Brieditis, I.; Raub-Segall, E.; Pol, E.; Hakansson, K.; Abrahamson, M., The importance of the second hairpin loop of cystatin C for proteinase binding, characterization of the interaction of Trp-106 variants of the inhibitor with cysteine proteinases. *Biochem.* 1996, 35 (33), 10720-10726.
30. Hamilton, G.; Colbert, J. D.; Schuettelkopf, A. W.; Watts, C., Cystatin F is a cathepsin C-directed protease inhibitor regulated by proteolysis. *EMBO J* 2008, 27 (3), 499-508.

31. Perry, R. D.; Sanclemente, C. L., Determination of Iron With Bathophenanthroline Following An Improved Procedure for Reduction of Iron(III) Ions. *Analyst* 1977, 102 (1211), 114-119.

The invention claimed is:

1. A multi-functional protease inhibitor conjugate molecule comprising a cystatin moiety and pepstatin A moiety, or a physiologically acceptable salt, solvate, ester, or amide thereof.

2. The multi-functional protease inhibitor according to claim 1 wherein the cystatin is cystatin C.

3. The multi-functional protease inhibitor according to claim 1 or 2 wherein the conjugate displays inhibitory activity against a cysteine proteinase and an aspartyl proteinase.

4. The multi-functional protease inhibitor according to claim 3 wherein the conjugate has inhibitory constants against said at least two proteinases with inhibitory constants smaller than 10 µM.

5. The multi-functional protease inhibitor according to claim 1 wherein the conjugate is soluble in aqueous solution with solubility greater than 50 nM, in aqueous buffer in the pH range of 3-10.

6. The multi-functional protease inhibitor according to claim 1, wherein a peptide moiety is incorporated between the cystatin moiety and the pepstatin A moiety of the multi-functional protease inhibitor conjugate molecule.

7. The multi-functional protease inhibitor according to claim 6, wherein the peptide moiety is hydrophilic or polar.

8. The multi-functional protease inhibitor according to claim 7, wherein the hydrophilic or polar peptide moiety is 2 to 30 amino acids in length.

9. The multi-functional protease inhibitor according to claim 6, wherein the peptide moiety comprises one or more targeting moieties to desired tissue or cell.

10. The multi-functional protease inhibitor according to claim 9 wherein the targeting peptide moiety is >4 amino acid residues long and comprises at least 2 amino acids with hydrophilic or polar side chains/or have hydrophilic and/or polar side chains.

11. The multi-functional protease inhibitor according to claim 10, wherein the amino acids in the targeting peptide are negatively charged at neutral pH.

12. The multi-functional protease inhibitor according to claim 10 wherein one or more of the amino acids in the targeting peptide comprises a side chain having an azido or alkyne functionality.

13. The multi-functional protease inhibitor according to claim 1 wherein conjugation of cystatin to pepstatin A is through a cysteine present on the cystatin molecule.

14. The multi-functional protease inhibitor according to claim 1, wherein the conjugation of cystatin to pepstatin A is through a lysine, or an amino acid having a side chain that has an azido or alkyne functionality.

15. The multi-functional protease inhibitor according to claim 1, wherein the cystatin is cystatin C and the residue to allow conjugation of cystatin to pepstatin A is threonine 102, or arginine 77, or Leucine 117, as numbered according to SEQ ID NO: 8.

16. The multi-functional protease inhibitor according to claim 15 wherein said residue is replaced with a cysteine residue.

17. A pharmaceutical composition comprising a multi-functional protease inhibitor conjugate molecule according to claim 1, comprising a pharmaceutically acceptable carrier.

18. A method of treatment of a disease selected from the group consisting of: cancer, inflammatory disease, autoimmune diseases, parasitic disease, galactosialidosis, and Gaucher's disease, said method comprising administering to a subject a pharmaceutical formulation comprising a multi-functional protease inhibitor conjugate molecule comprising a cystatin moiety and pepstatin A moiety, or a physiologically acceptable salt, solvate, ester, or amide thereof.

19. A vaccine comprising a multi-functional protease inhibitor conjugate molecule comprising a cystatin moiety and pepstatin A moiety, or a physiologically acceptable salt, solvate, ester, or amide thereof.

20. A method of wound healing, comprising administering to a subject a pharmaceutical formulation comprising a multi-functional protease inhibitor conjugate molecule comprising a cystatin moiety and pepstatin A moiety, or a physiologically acceptable salt, solvate, ester, or amide thereof, together with one or more growth factors.

21. The multi-functional protease inhibitor according to claim 5 wherein the conjugate is soluble in aqueous solution with solubility greater than 500 nM.

22. The multi-functional protease inhibitor according to claim 5 wherein the conjugate is soluble in aqueous solution with solubility greater than 1 μM.

23. The multi-functional protease inhibitor according to claim 10, wherein the amino acids in the targeting peptide comprise a hydroxyl side chain or a carboxylic acid side chain.

* * * * *